(12) United States Patent
Stalsberg et al.

(10) Patent No.: US 7,765,004 B2
(45) Date of Patent: Jul. 27, 2010

(54) METHODS AND SYSTEMS FOR MANAGING FUSION AND NOISE IN CARDIAC PACING RESPONSE CLASSIFICATION

(75) Inventors: Kevin John Stalsberg, White Bear Lake, MN (US); Yanting Dong, Shoreview, MN (US); Scott A. Meyer, Rochester, MN (US); John Michael Voegele, Bethel, MN (US); Derek Daniel Bohn, Woodbury, MN (US); Eric Keith Enrooth, Lino Lakes, MN (US); Clayton Scott Foster, Andover, MN (US); David William Yost, Brooklyn Park, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 381 days.

(21) Appl. No.: 11/116,565

(22) Filed: Apr. 28, 2005

(65) Prior Publication Data
US 2006/0247695 A1 Nov. 2, 2006

(51) Int. Cl.
*A61N 1/08* (2006.01)
(52) U.S. Cl. ...................................................... 607/28
(58) Field of Classification Search ............. 607/27–28
See application file for complete search history.

(56) References Cited

U.S. PATENT DOCUMENTS

| 3,920,005 A | 11/1975 | Gombrich et al. |
| 4,878,497 A | 11/1989 | Callaghan et al. |
| 5,222,493 A | 6/1993 | Sholder |
| 5,271,411 A | 12/1993 | Ripley et al. |
| 5,324,310 A | 6/1994 | Greeninger et al. |
| 5,350,410 A | 9/1994 | Kleks et al. |
| 5,431,693 A * | 7/1995 | Schroeppel ............. 607/28 |
| 5,443,485 A * | 8/1995 | Housworth et al. ....... 607/28 |
| 5,522,860 A | 6/1996 | Molin et al. |

(Continued)

FOREIGN PATENT DOCUMENTS

EP 468720 1/1992

(Continued)

OTHER PUBLICATIONS

Splett et al. "Determination of Pacing Capture in Implantable Defibrillators: Benefit of Evoked Response Detection Using RV Coil to Can Vector," PACE, vol. 23, pp. 1645-1650, Nov. 2000.

(Continued)

*Primary Examiner*—Mark W Bockelman
*Assistant Examiner*—Eric D. Bertram
(74) *Attorney, Agent, or Firm*—Hollingsworth & Funk, LLC

(57) ABSTRACT

Methods and systems for detecting noise in cardiac pacing response classification processes involve determining that a cardiac response classification is possibly erroneous if unexpected signal content is detected. The unexpected signal content may comprise signal peaks that have polarity opposite to the polarity of peaks used to determine the cardiac response to pacing. Fusion/noise management processes include pacing at a relatively high energy level until capture is detected after a fusion, indeterminate, or possibly erroneous pacing response classification is made. The relatively high energy pacing pulses may be delivered until capture is detected or until a predetermined number of paces are delivered.

35 Claims, 14 Drawing Sheets

U.S. PATENT DOCUMENTS

| | | | |
|---|---|---|---|
| 5,626,620 A | 5/1997 | Kieval et al. | |
| 5,683,431 A | 11/1997 | Wang | |
| 5,683,434 A | 11/1997 | Archer | |
| 6,038,474 A | 3/2000 | Zhu et al. | |
| 6,101,416 A | 8/2000 | Sloman | |
| 6,128,535 A | 10/2000 | Maarse | |
| 6,148,234 A | 11/2000 | Struble | |
| 6,163,724 A | 12/2000 | Hemming et al. | |
| 6,169,921 B1 | 1/2001 | KenKnight et al. | |
| 6,175,766 B1 | 1/2001 | Bornzin et al. | |
| 6,192,275 B1 | 2/2001 | Zhu et al. | |
| 6,226,551 B1 | 5/2001 | Zhu et al. | |
| 6,238,419 B1 | 5/2001 | Lindgren | |
| 6,275,731 B1 | 8/2001 | Zhu et al. | |
| 6,324,427 B1 | 11/2001 | Florio | |
| 6,345,201 B1 | 2/2002 | Sloman et al. | |
| 6,434,428 B1 | 8/2002 | Sloman et al. | |
| 6,449,503 B1 | 9/2002 | Hsu | |
| 6,456,881 B1 | 9/2002 | Bornzin et al. | |
| 6,466,820 B1 | 10/2002 | Juran et al. | |
| 6,477,422 B1 | 11/2002 | Splett | |
| 6,505,071 B1 | 1/2003 | Zhu et al. | |
| 6,512,953 B2 | 1/2003 | Florio et al. | |
| 6,567,701 B2 | 5/2003 | Vonk | |
| 6,615,082 B1 | 9/2003 | Mandell | |
| 6,618,619 B1 | 9/2003 | Florio et al. | |
| 6,654,637 B2 | 11/2003 | Rouw et al. | |
| 6,738,669 B1 | 5/2004 | Sloman et al. | |
| 6,768,924 B2 | 7/2004 | Ding et al. | |
| 6,881,192 B1 | 4/2005 | Park | |
| 6,885,893 B1 | 4/2005 | Lu | |
| 6,944,495 B2 | 9/2005 | MacAdam et al. | |
| 6,950,702 B2 | 9/2005 | Sweeney | |
| 6,959,214 B2 | 10/2005 | Pape et al. | |
| 6,961,613 B2 | 11/2005 | Bjorling et al. | |
| 6,973,350 B1 | 12/2005 | Levine et al. | |
| 6,975,904 B1 | 12/2005 | Sloman | |
| 6,999,817 B2 | 2/2006 | Park et al. | |
| 7,027,868 B2 | 4/2006 | Rueter et al. | |
| 7,117,036 B2 | 10/2006 | Florio | |
| 7,139,610 B2 | 11/2006 | Ferek-Petric | |
| 7,191,004 B2 | 3/2007 | Kim et al. | |
| 7,203,542 B2 | 4/2007 | Obel | |
| 7,203,543 B2 | 4/2007 | Meyer et al. | |
| 7,212,862 B2 | 5/2007 | Park et al | |
| 7,248,921 B2 | 7/2007 | Palreddy et al. | |
| 7,319,900 B2 | 1/2008 | Kim et al. | |
| 2002/0095188 A1 | 7/2002 | Mower | |
| 2002/0138111 A1 | 9/2002 | Greenhut et al. | |
| 2002/0183798 A1 | 12/2002 | Vonk | |
| 2003/0050671 A1 | 3/2003 | Bradley | |
| 2003/0083710 A1 | 5/2003 | Ternes et al. | |
| 2003/0083711 A1* | 5/2003 | Yonce et al. | 607/27 |
| 2004/0127950 A1* | 7/2004 | Kim et al. | 607/27 |
| 2004/0171959 A1 | 9/2004 | Staler et al. | |
| 2004/0172065 A1 | 9/2004 | Sih et al. | |
| 2004/0215277 A1 | 10/2004 | Oosterhoff et al. | |
| 2004/0243014 A1 | 12/2004 | Lee et al. | |
| 2004/0260351 A1 | 12/2004 | Holmstrom et al. | |
| 2005/0004612 A1 | 1/2005 | Scholten et al. | |
| 2005/0131476 A1 | 6/2005 | Kim et al. | |
| 2005/0131477 A1 | 6/2005 | Meyer et al. | |
| 2006/0241706 A1 | 10/2006 | Yonce et al. | |
| 2007/0016261 A1 | 1/2007 | Dong et al. | |

FOREIGN PATENT DOCUMENTS

| | | |
|---|---|---|
| EP | 1291038 | 3/2003 |
| WO | WO9904841 | 4/1999 |
| WO | WO0017615 | 3/2000 |
| WO | WO02087696 | 11/2002 |
| WO | WO2004026398 | 4/2004 |
| WO | WO2005058412 | 6/2005 |

OTHER PUBLICATIONS

Cohen et al. Capture Management Efficacy in children and young adults with endocardial and unipolar epicardial systems. Europace, vol. 6, pp. 248-255, 2004.

* cited by examiner

METHODS AND SYSTEMS FOR MANAGING FUSION AND NOISE IN CARDIAC PACING RESPONSE CLASSIFICATION

FIELD OF THE INVENTION

The present invention relates generally to implantable medical devices and, more particularly, to noise detection and fusion/noise management techniques implemented in connection with cardiac response classification.

BACKGROUND OF THE INVENTION

When functioning normally, the heart produces rhythmic contractions and is capable of pumping blood throughout the body. However, due to disease or injury, the heart rhythm may become irregular resulting in diminished pumping efficiency. Arrhythmia is a general term used to describe heart rhythm irregularities arising from a variety of physical conditions and disease processes. Cardiac rhythm management systems, such as implantable pacemakers and cardiac defibrillators, have been used as an effective treatment for patients with serious arrhythmias. These systems typically comprise circuitry to sense electrical signals from the heart and a pulse generator for delivering electrical stimulation pulses to the heart. Leads extending into the patient's heart are connected to electrodes that contact the myocardium for sensing the heart's electrical signals and for delivering stimulation pulses to the heart in accordance with various therapies for treating the arrhythmias.

Cardiac rhythm management systems operate to stimulate the heart tissue adjacent to the electrodes to produce a contraction of the tissue. Pacemakers are cardiac rhythm management systems that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

When a pace pulse produces a contraction in the heart tissue, the electrical cardiac signal preceding the contraction is denoted the captured response (CR). The captured response typically includes an electrical signal, denoted the evoked response signal, associated with the heart contraction, along with a superimposed signal associated with residual post pace polarization at the electrode-tissue interface. The magnitude of the residual post pace polarization signal, or pacing artifact, may be affected by a variety of factors including lead polarization, after-potential from the pace pulse, lead impedance, patient impedance, pace pulse width, and pace pulse amplitude, for example.

A pace pulse must exceed a minimum energy value, or capture threshold, to produce a contraction. It is desirable for a pace pulse to have sufficient energy to stimulate capture of the heart without expending energy significantly in excess of the capture threshold. Thus, accurate determination of the capture threshold is required for efficient pace energy management. If the pace pulse energy is too low, the pace pulses may not reliably produce a contractile response in the heart and may result in ineffective pacing. If the pace pulse energy is too high, the patient may experience discomfort and the battery life of the device will be shorter.

Detecting if a pacing pulse "captures" the heart and produces a contraction allows the cardiac rhythm management system to adjust the energy level of pace pulses to correspond to the optimum energy expenditure that reliably produces capture. Further, capture detection allows the cardiac rhythm management system to initiate a back-up pulse at a higher energy level whenever a pace pulse does not produce a contraction.

A fusion beat is a cardiac contraction that occurs when two cardiac depolarizations of a particular chamber, but from separate initiation sites, merge. At times, a depolarization initiated by a pacing pulse may merge with an intrinsic beat, producing a fusion beat. Fusion beats, as seen on electrocardiographic recordings, exhibit various morphologies. The merging depolarizations of a fusion beat do not contribute evenly to the total depolarization.

Pseudofusion occurs when a pacing stimulus is delivered on a spontaneous P wave during atrial pacing or on a spontaneous QRS complex during ventricular pacing. In pseudofusion, the pacing stimulus may be ineffective because the tissue around the electrode has already spontaneously depolarized and is in its refractory period.

Noise presents a problem in capture detection processes when the pacemaker mistakenly identifies noise as capture, fusion/pseudofusion, or intrinsic activity. Noise mistakenly identified as capture or fusion/pseudofusion may cause a pacemaker to erroneously withhold backup pacing under loss of capture conditions. Noise mistakenly identified as early intrinsic activity may lead to a premature loss of capture determination during threshold testing. The present invention provides methods and systems for identifying and managing fusion and/or noise in capture determination processes.

SUMMARY OF THE INVENTION

The present invention involves various methods and systems directed to noise detection and fusion/noise management techniques for cardiac response classification. One embodiment of the invention involves a method for detecting cardiac signal noise during capture verification. The method includes delivering a pacing pulse to a heart chamber. A cardiac signal associated with the pacing pulse is sensed. The cardiac response to the pacing pulse is classified based on the sensed cardiac signal. If unexpected signal content is detected in the cardiac signal, then the cardiac response classification is determined to be possibly erroneous.

In accordance with another embodiment of the invention, a method involves a method for managing fusion, indeterminate or possibly erroneous pacing responses, comprising. A first pacing pulse is delivered to a heart chamber. One or more pacing pulses are delivered to the heart chamber if the cardiac response associated with the first pacing pulse is at least one of fusion, indeterminate and possibly erroneous. The one or more pacing pulses have a pacing energy greater than the first pacing pulse. One or more cardiac pacing responses respectively associated with the one or more pacing pulses are determined. The one or more pacing pulses continue to be delivered if each of the one or more cardiac pacing responses is at least one of fusion, indeterminate, and possibly erroneous.

Yet another embodiment of the invention comprises a cardiac signal noise detection method. A cardiac signal is sensed in one or more classification intervals following the delivery of a pacing pulse. The cardiac signal sensed in the one or more classification intervals is used to classify a cardiac response to the pacing pulse. The cardiac signal is sensed in a noise detection interval following the classification intervals. Noise is detected based on the cardiac signal sensed in at least one of the one or more classification intervals and the noise detection interval.

Another embodiment of the invention comprises a cardiac rhythm management device. The cardiac rhythm management device includes a pulse generator configured to deliver pacing pulses to a heart chamber and a sensing circuit configured to sense cardiac signals of the heart chamber associated with the pacing pulses. A cardiac response classification processor is coupled to the sensing circuit. The processor is configured to classify a cardiac response to a pacing pulse based on a sensed cardiac signal associated with the pacing pulse. The processor is further configured to determine that the cardiac response classification is possibly erroneous if unexpected signal content is detected on the sensed cardiac signal.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
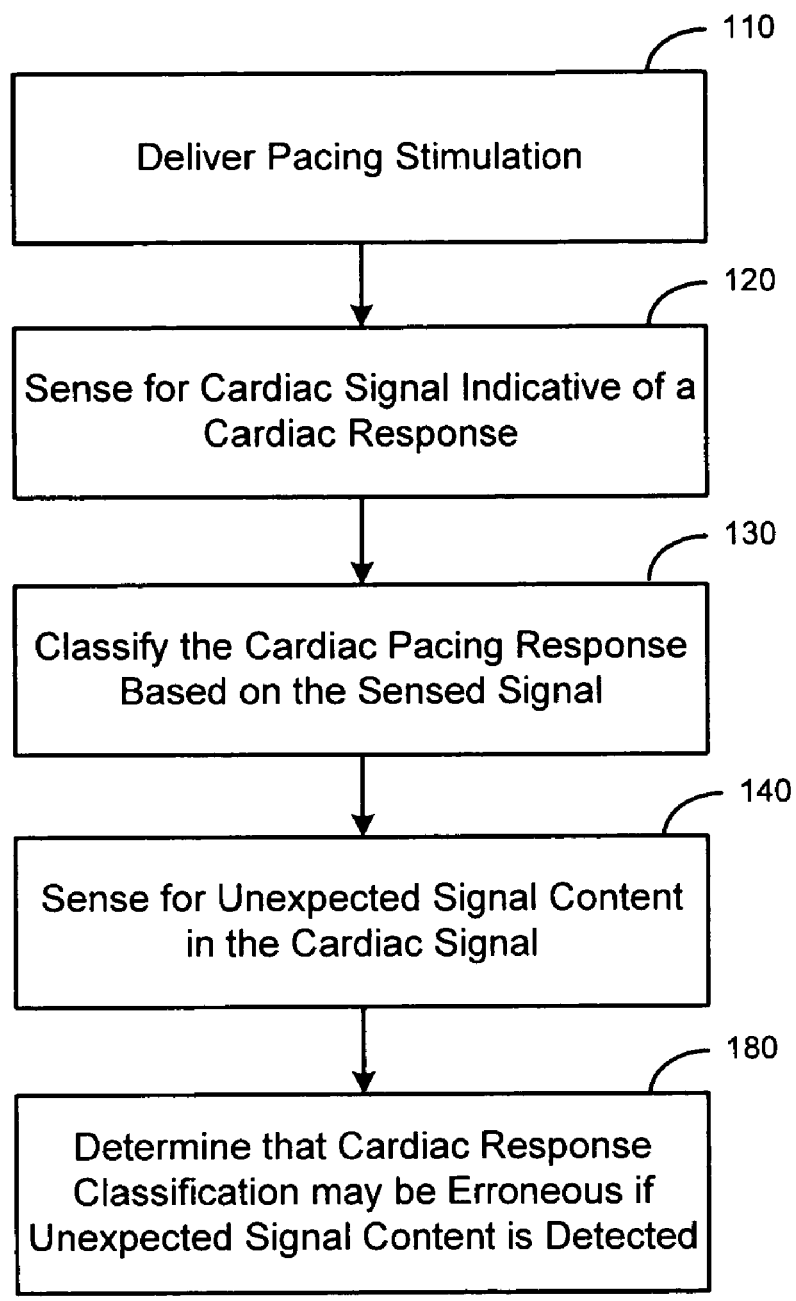
FIG. 1 is a flowchart of a method of detecting noise during cardiac response classification in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

Cardiac response classification may be implemented by a pacemaker or other cardiac rhythm management (CRM) device to determine whether an applied electrical pacing stimulus captures the heart. Embodiments of the invention are directed to methods and systems that reduce the misclassification and impact of noise in capture determination processes. The capture detection methods described herein use signal features to discriminate between various cardiac responses to pacing, including noncapture, capture, fusion/pseudofusion, and noncapture with intrinsic activity.

A noisy signal sensed following the pacing pulse may cause the pacemaker to erroneously classify the cardiac pacing response. For example, a noise signal may have features similar to a captured response, a fusion/pseudofusion beat, or early intrinsic activation. An erroneous classification of noise as capture or fusion/pseudofusion may cause the pacemaker to withhold backup pacing under loss of capture conditions. Methods and systems of the present invention reduce the possibility of mistakenly identifying noise as capture or fusion/pseudofusion. Further, fusion/noise management techniques in accordance with embodiments of the invention provide continued backup pacing if a cardiac response classification is possibly erroneous.

Noise may be mistakenly identified as early intrinsic activity. Mistaking noise as early intrinsic activity may cause the pacemaker to erroneously detect loss of capture. The misclassification of noise as early intrinsic activity during capture threshold testing may lead to inaccurate threshold identification. Methods and systems of the present invention reduce the possibility of mistakenly identifying noise as early intrinsic activation.

In accordance with various embodiments of the invention, noise discrimination relies on a relatively consistent morphology of captured, early intrinsic, and/or fusion beats. Noise discrimination methods in accordance with embodiments of the invention involve sensing for unexpected signal content that is present during the cardiac response classification process. In one implementation, the pacemaker senses for evidence of noise during the same time interval that the pacemaker senses for signal features that are used to determine the cardiac pacing response. In another implementation, the pacemaker senses for noise in a separate noise interval.

A method of detecting noise during a cardiac response classification according to embodiments of the invention is illustrated in the flow chart of FIG. 1. A pacing pulse is delivered 110 to a heart chamber. The system senses for 120 a cardiac signal indicative of a cardiac response to the pacing pulse. The cardiac pacing response is classified 130 based on the sensed cardiac signal.

The system senses for 140 unexpected signal content. The unexpected signal content may include, for example, cardiac signal peaks or other features that are inconsistent with an expected cardiac response such as capture, fusion/pseudofusion, or noncapture with intrinsic activation. If the unexpected signal content is detected 180, then the system determines that the cardiac response classification is possibly erroneous.

The cardiac signal following a pacing pulse may be sensed in one or more time intervals to determine the cardiac response to the pacing pulse. In some embodiments, classification of the cardiac response to the pacing pulse is based on the peak value and peak timing of the cardiac signal in one or more time intervals following pacing. Unexpected signal content may comprise cardiac signal peaks having opposite polarity from the polarity of the peaks used for cardiac response classification.

Figure 2:
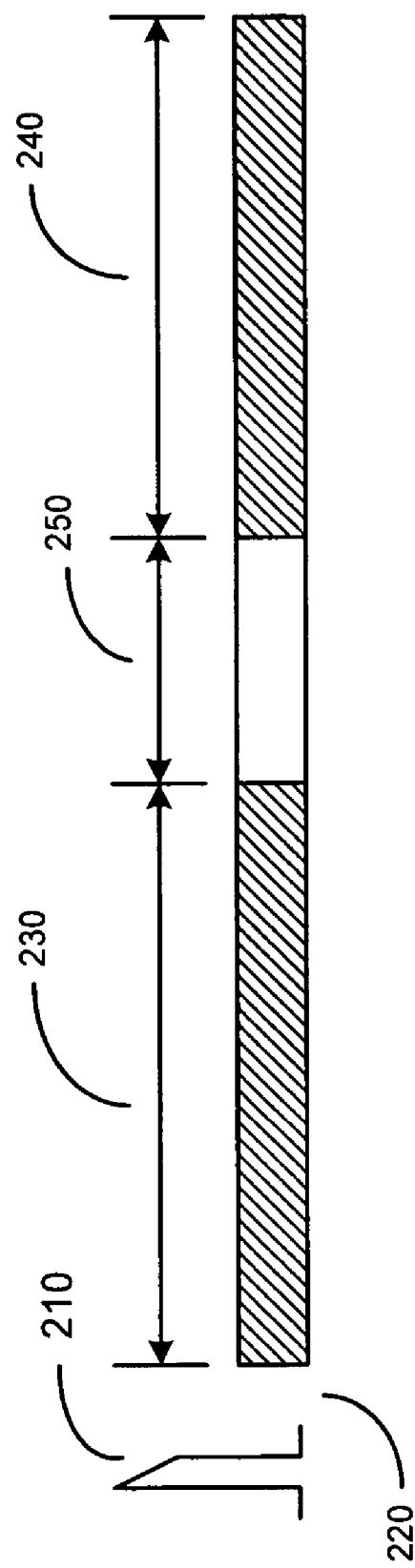
FIG. 2 is a diagram illustrating time intervals that may be used for cardiac response classification in accordance with embodiments of the invention.

FIG. 2 is a diagram illustrating multiple time intervals that may be used for cardiac response classification in accordance with embodiments of the invention. A pacing stimulation 210 is delivered to the heart, for example, to the right ventricle. The cardiac signal is blanked for a period of time 220, typically about 0 ms to about 40 ms, following the delivery of the pacing stimulation 210. After the blanking period 220, a first time interval 230 is initiated. The length of the first time interval 230 may be a programmable length, for example, less than about 325 ms. The cardiac signal associated with the pacing pulse is sensed during the first time interval 230. If the cardiac signal does not exceed a threshold in the first time interval 230, then the cardiac response may be classified as a noncaptured response. If the cardiac signal exceeds a threshold value, then various features of the cardiac signal may be detected and used for cardiac response classification. In some cases, sensing of the cardiac signal may be extended to additional time intervals, such as the second time interval 240. The length of the second time interval 240 may be programmable, and may have a length less than about 325 ms. The additional time intervals may be triggered by events occurring in the first time interval, such as if features of the cardiac signal are detected or are not detected in the first time interval. The length of the additional time intervals may be different or the same as the length of the first time interval. Alternatively, the lengths of the first and the additional time intervals may be the same.

A delay period 250 may be established between the end of one time interval 230 and the beginning of another time interval 240. The length of the delay may be in a range of about 0 ms (no delay) to about 40 ms, for example. The cardiac response to the pacing stimulation 210 may be classified based on characteristics of the cardiac signal sensed in the first and/or the additional time intervals 230, 240.

Figure 3A:
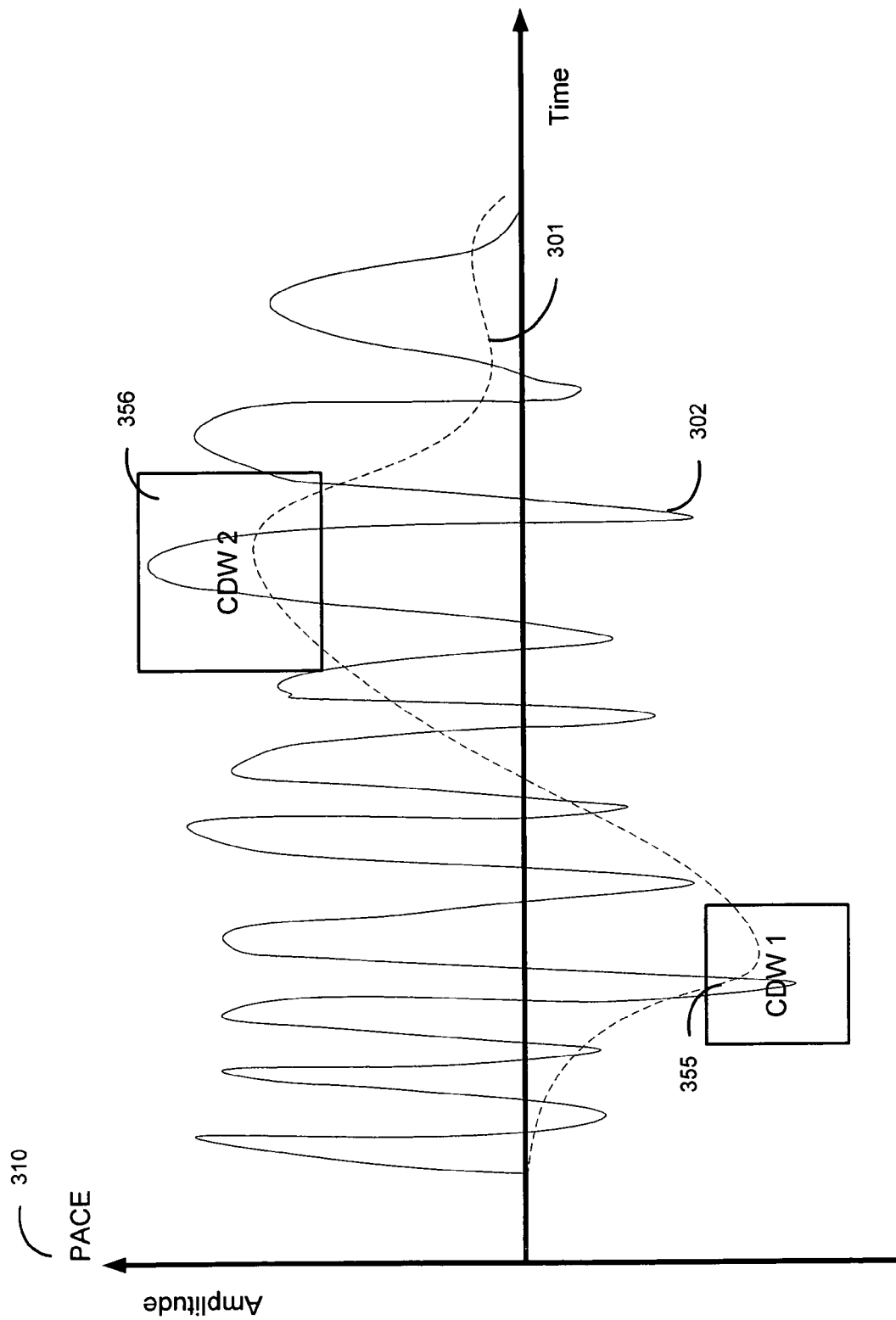
FIG. 3A illustrates a cardiac signal indicative of a captured response superimposed on a noncaptured signal affected by noise.

FIG. 3A illustrates a cardiac signal indicative of a captured response 301 superimposed on a noncaptured signal affected by noise 302. The signal morphologies associated with captured beats, fusion/pseudofusion beats, and early intrinsic beats are relatively consistent. Cardiac response classification may be performed by determining if peaks of the cardiac signal following a pacing pulse fall into cardiac response classification windows associated with capture, fusion, or early intrinsic activity. FIG. 3A illustrates a captured response signal 301 following a pacing pulse 310. The captured response signal 301 has peaks that fall within the first and second classification windows 355, 356.

A noisy signal 302 may mimic a legitimate cardiac pacing response. The noisy cardiac signal 302 may also have peaks that fall within the cardiac response classification windows 355, 356 leading to erroneous classification of the cardiac response.

Figure 3B:
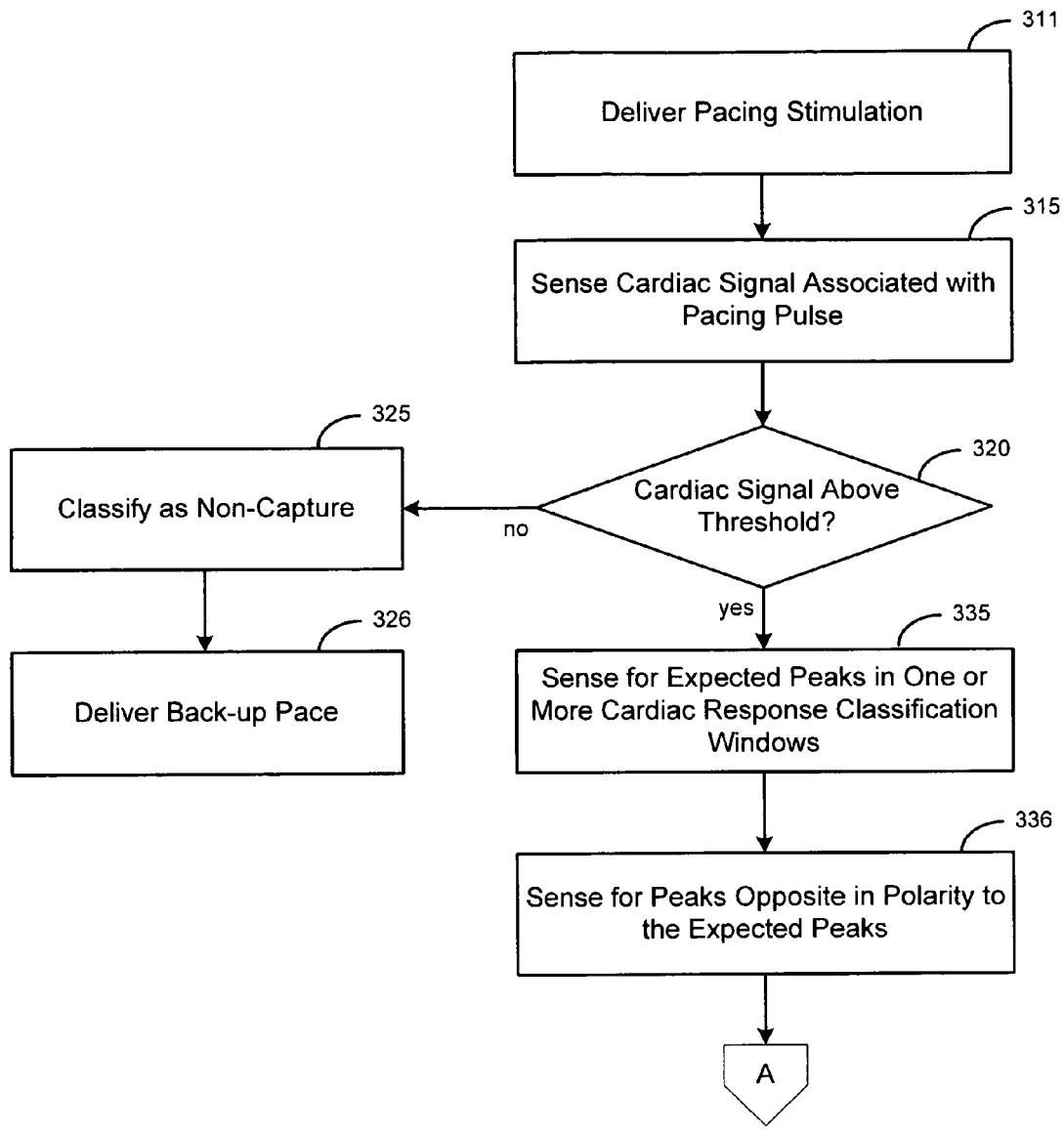
FIGS. 3B and 3C are flowcharts illustrating a method of using noise detection windows for determining if a cardiac signal is noisy and if cardiac response classification would yield a possibly erroneous result in accordance with embodiments of the invention.

In accordance with embodiments of the invention, one or more noise detection windows may be used to determine if a cardiac response classification is legitimate, or if the cardiac response classification is possibly erroneous due to noise. The flowcharts of FIGS. 3B and 3C illustrate a method for using noise detection windows for determining if a cardiac signal is noisy and if cardiac response classification has produced a possibly erroneous result.

After delivering a pacing pulse 311, the system senses 315 the cardiac signal associated with the pacing pulse. If the cardiac signal magnitude does not exceed 320 a threshold value in the first time interval, then the response to pacing is determined to be 325 noncapture. A backup pace 326 may be delivered.

If the cardiac signal exceeds 320 the threshold value, then the system senses for 335 an expected cardiac signal peak value in one or more classification windows. The expected cardiac signal peaks may be used to discriminate capture, fusion/pseudofusion, and/or intrinsic activation. The system also senses for 336 one or more peaks that are opposite in polarity and comparable in magnitude to the expected cardiac signal peaks.

Figure 3C:
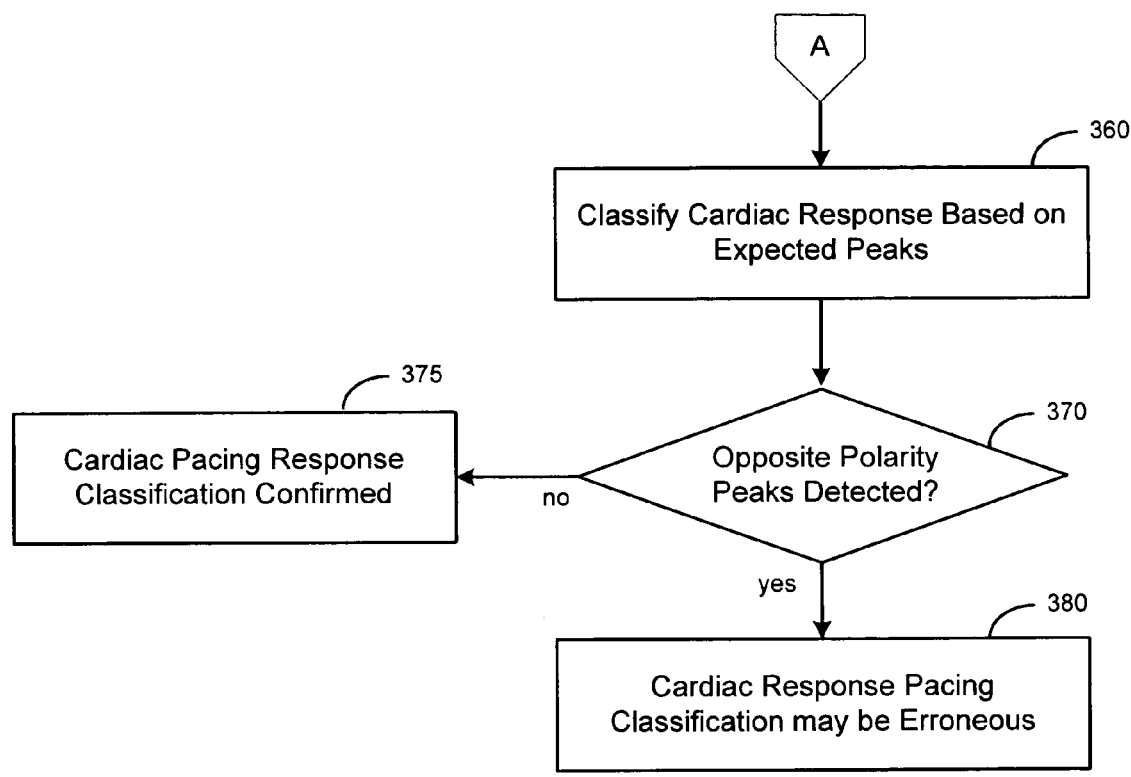

Continuing to FIG. 3C, the system classifies 360 the cardiac pacing response based on one or more cardiac signal peaks detected in the one or more classification windows. If the unexpected signal content was detected 370 at block 336, then the cardiac signal is determined to be noisy and classification of the cardiac response is possibly 380 an erroneous classification. If opposite polarity peaks were not detected 370, then the cardiac signal is not noisy and the cardiac response to pacing is confirmed 375.

Figure 4:
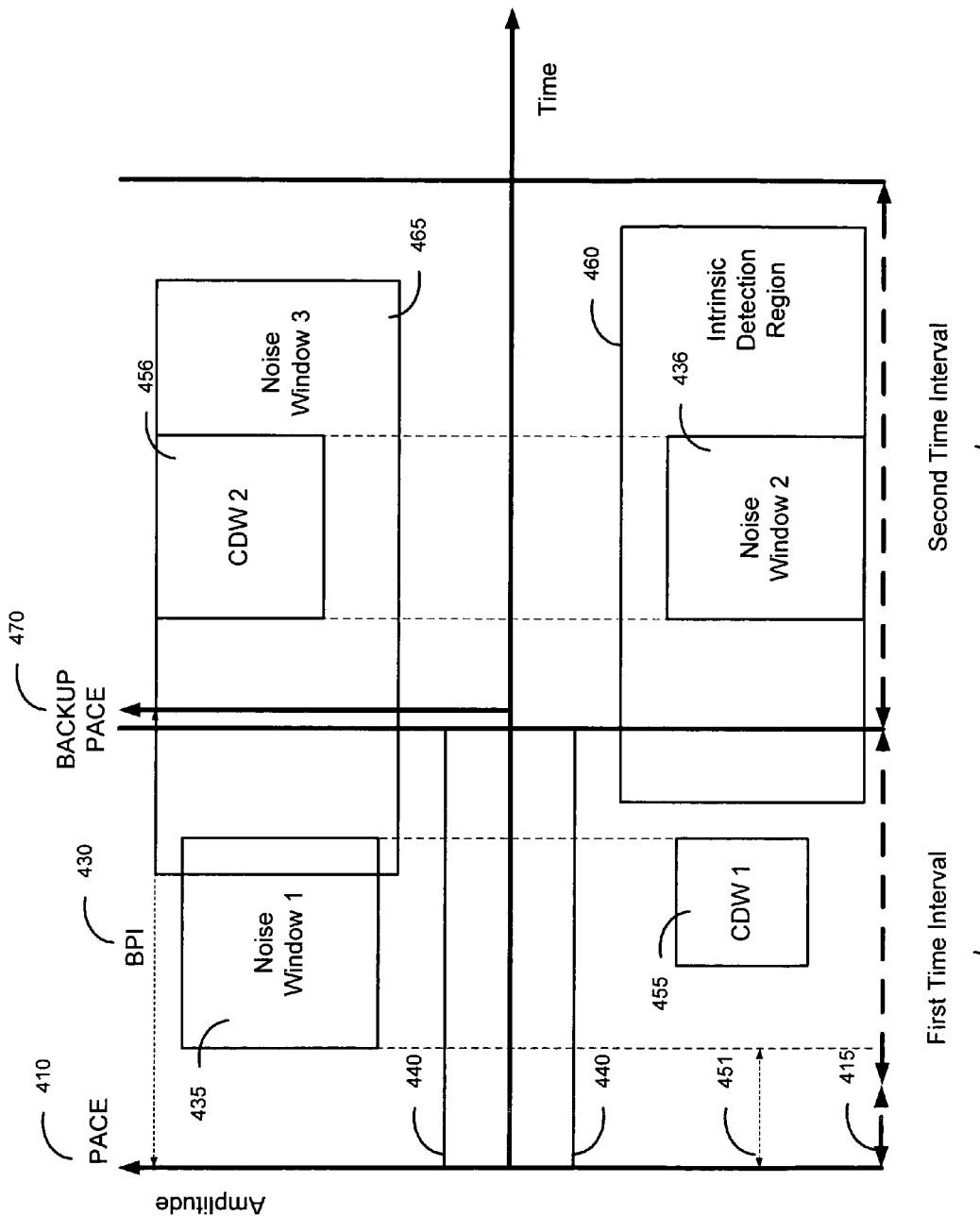
FIG. 4 illustrates cardiac response classification windows and noise detection windows that may be utilized for noise detection in accordance with embodiments of the invention.

FIG. 4 illustrates cardiac response classification windows and noise detection windows that may be utilized for noise detection in accordance with embodiments of the invention. Following delivery of a pacing pulse 410, the sensing system is blanked, e.g., the sense electrodes are disconnected from sense amplifiers or the sense amplifiers are rendered inoperative, during a blanking period 415.

Following the blanking period, the cardiac signal is sensed in one or more time intervals. As illustrated in FIG. 4, sensing may occur in two time intervals 420, 450 following the pacing pulse 410. In some scenarios, the second 450 and subsequent time intervals (not shown) may be triggered by events occurring in one or more previous intervals. In various implementations, sensing may be performed using the same electrode combination that was used to deliver the pacing stimulation. In other implementations, the pacing stimulation may be delivered using a first electrode configuration and sensing may use a second electrode configuration. Systems and methods for classifying a cardiac response to pacing using multiple time intervals and various sensing and pacing vectors are described in commonly owned U.S. Pat. No. 7,319,900, now U.S. Patent Publication No. 2005/0131477, and U.S. Patent Publication No. 2005/0131478, which are incorporated herein by reference.

During the first time interval 420, the system senses for a cardiac signal magnitude above a threshold level 440. If the cardiac signal does not exceed the threshold 440 during the first time interval 420, then the cardiac response is classified as noncapture and a backup pace 470 may be delivered. The backup pace 470 is typically a high energy pace that is delivered following a backup interval 430. For example, the backup interval 430 may comprise an interval of about 100 ms timed from the delivery of the primary pacing pulse 410.

The system may utilize one or more cardiac response classification windows 455, 456, 460 as illustrated in FIG. 4. A cardiac response classification method in accordance with embodiments of the invention involves determining if one or more peak values of the cardiac signal fall within one or more cardiac response classification windows 455, 456, 460. The cardiac response classification windows 455, 456, 460 are areas defined in terms of amplitude and time in one or more time intervals 420, 450 following the pacing pulse. For example, the system may classify a cardiac response as capture if a peak value of the cardiac signal in the first time interval 420 is detected in the first capture detection window 455 and a peak value of the cardiac signal in the second time interval 450 is detected in the second capture detection window 456. If a first cardiac signal peak is detected in the first classification window 455, and the second cardiac signal peak misses the second capture detection window 456, then the cardiac response may be classified as a fusion/pseudofusion beat. If a cardiac signal peak occurring in the first or the second time intervals 420, 450 is detected in the intrinsic detection window 460, the cardiac response may be classified as noncapture with early intrinsic activation.

In some scenarios, noise may cause signal peaks to be detected in the first and/or the second capture detection windows 455, 456, causing the signal to erroneously classify the cardiac response as capture or fusion/pseudofusion. Further, a cardiac signal peak may be detected in the intrinsic detection window 460, causing an erroneous classification of noncapture with intrinsic activation.

A noise detection methodology in accordance with embodiments of the present invention involves the use of one or more noise detection windows 435, 436, 465 for determining if the cardiac signal is noisy. A first noise detection window 435 is associated with a first capture detection window 455, a second noise detection window 436 is associated with a second capture detection window 456, and a third noise detection window 465 is associated with the intrinsic detection window 460. If signal peaks fall within the cardiac response classification windows 455, 456, 460, then the system checks for peaks opposite in polarity and comparable in magnitude to the cardiac response signal peaks. FIG. 4 illustrates noise detection windows 435, 436, 465 in the first and the second time intervals 420, 450. The noise detection windows 435, 436, 465 may be any shape or size. For example, the noise detection windows 435, 436 may be the same size and/or shape as a corresponding capture detection window 455, 456 in a particular time interval 420, 450, or may be a different size and/or shape.

In some implementations, the dimensions of the noise detection windows 435, 436, 465 may be related to the dimensions of the corresponding cardiac response detection windows 455, 456, 460. For example, in one implementation, a noise detection window may have time dimensions equal to the time dimensions of a corresponding cardiac response detection window. The noise detection window may have amplitude dimensions equal in magnitude but opposite in sign to the amplitude dimensions of the corresponding cardiac response detection window. In another implementation, the dimensions of a noise detection window may be related to features detected in a cardiac response classification window. For example, the end of the third noise detection window 465 may correspond to the timing of the peak detected in the intrinsic detection window 460. In this example, if the system determines that the cardiac pacing response is noncapture with intrinsic activity based on a peak detected in the intrinsic detection window 460, then the system may sense for noise in a noise detection window that extends to the time of the detected intrinsic peak.

In an example of noise detection for an early intrinsic response, once conditions are satisfied for early intrinsic classification, the system checks for unexpected signal behavior. In the case of an early intrinsic response, a substantial positive peak before the negative peak that lands in the early intrinsic window would be considered unexpected signal content. If this unexpected signal content is observed, then an erroneous intrinsic response classification is likely.

The details of the noise check after early intrinsic detection are that in the first time interval 420, the system checks if a positive peak was detected between about 40 ms past the primary pacing pulse 410 and the minimum of the time of the negative peak that landed in the intrinsic detection region 460 or the end of the first time interval 420, and that the peak amplitude was greater than about 0.7 times the amplitude of the negative peak that landed in the intrinsic detection region 460, yet no less than the detection threshold 440. If these conditions are met, the system determines that noise is present and determines that the early intrinsic classification is likely to be erroneous. In this scenario, the cycle is handled as if it were a fusion/indeterminate beat. The 40 ms timing results from the consideration that under certain circumstances the pacing artifact can be greater than 2 mV until about 30-35 ms post pace and this should not be considered noise.

The classification windows 455, 456, 460 may be formed using one or more cardiac signals representative of a particular type of cardiac response. For example, capture detection windows 455, 456 may be formed based on the peaks of one or more captured responses. The intrinsic detection window 460 may be formed using peaks of one or more cardiac signals representative of intrinsic activation.

Classification detection windows used to detect peaks of a cardiac signal associated with a particular type of cardiac pacing response may be adapted to accommodate gradual morphological changes in the patient's pacing response signal. A cardiac signal waveform, e.g., a cardiac signal waveform representative of a captured response, may exhibit natural variations in its morphology over time. Unless the capture detection windows 455, 456 are adjusted, the captured beat morphology may gradually drift away from the originally established capture detection windows 455, 456 used to recognize capture. Similarly, the intrinsic detection window 460 may be adapted based on changes in the intrinsic activation morphology.

In accordance with embodiments of the invention, one or more of the classification detection windows 455, 456, 460 may be adjusted to accommodate changes in cardiac waveform morphology. A particular detection window may be adjusted according to a relationship, e.g., a spatial relationship, between the particular detection window and a corresponding waveform feature of a detected cardiac signal, for example, a peak of the cardiac signal. Adjustment of the detection windows may involve, for example, changing the size, shape, or location of the detection window.

As previously discussed, a noise detection window may be associated with a particular classification detection window. In this scenario, if the particular classification detection window is adapted over time, the associated noise detection window may be correspondingly adapted. For example, if the magnitude of a first capture detection window 455 is adjusted in the direction of a more negative magnitude, the first noise detection window 435 may be correspondingly adjusted in the direction of a more positive magnitude. If the first capture detection window 455 is adjusted in the positive time direction, the first noise detection window 435 may be correspondingly adjusted in the positive time direction.

Methods and systems for forming and adapting cardiac response classification detection windows, aspects of which may be utilized in embodiments of the present invention, are described in commonly owned U.S. Pat. No. 7,477,932, U.S. Pat. No. 7,499,751, and U.S. Pat. No. 7,574,260, each of which are incorporated herein by reference.

The noise discrimination processes discussed above involve sensing for unexpected signal content contemporaneously with sensing for cardiac signal features used for classifying the cardiac pacing response. Other implementations involve sensing for unexpected noise content in a time interval that occurs after the time interval used to sense for the signal features that are used to classify the cardiac response. In various embodiments, the system may sense for noise during a quiescent period following one or more time intervals used to detect signal features for cardiac response classification.

Figure 5:
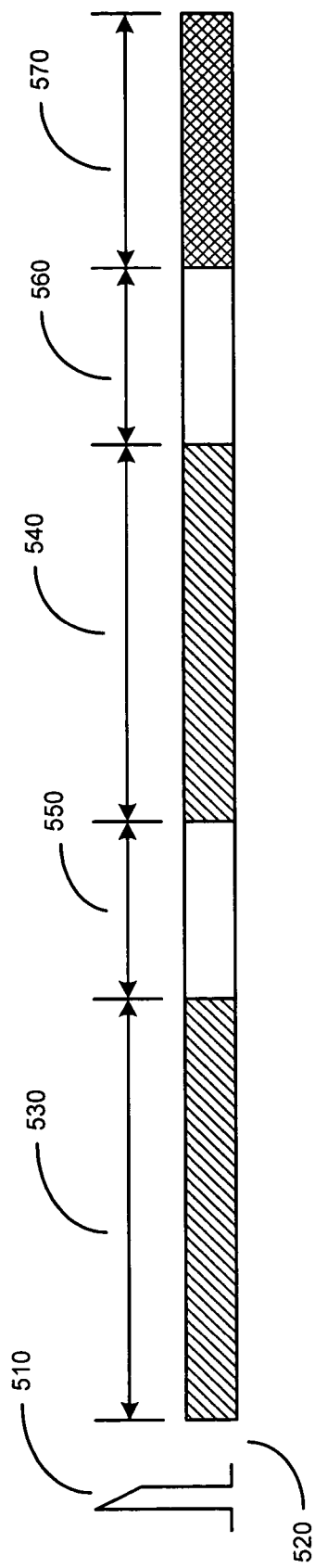
FIG. 5 illustrates timing intervals that may be used for noise detection according to embodiments of the invention.

FIG. 5 illustrates timing intervals that may be used for noise detection according to embodiments of the invention. A pacing stimulation 510 is delivered to the heart, for example, to the right ventricle. The cardiac signal is blanked for a period of time 520, e.g., about 0 ms to about 40 ms, following the delivery of the pacing stimulation 510. After the blanking period 520, the cardiac signal associated with the pacing pulse is sensed during a first time interval 530. If the cardiac signal does not exceed a threshold in the first time interval 530, then the cardiac response may be classified as a noncaptured response. If the cardiac signal exceeds the threshold value, then the cardiac signal may be sensed in one or more additional time intervals, such as a second time interval 540. Although FIG. 5 shows two time intervals used to sense for cardiac signal features indicative of a cardiac pacing response, any number of intervals may be used. In some embodiments, the second and subsequent time intervals may be triggered by events occurring in one or more previous time intervals.

A delay period 550 may be established between two successive time intervals. The length of the delay may be in a range of about 0 ms (no delay) to about 40 ms, for example. The cardiac response to the pacing stimulation 510 may be classified based on characteristics of the cardiac signal sensed in the first and/or the second time intervals.

As illustrated in FIG. 5, one or more noise detection intervals 570 may follow the cardiac response classification intervals 530, 540. The noise detection interval 570 may be separated from the last classification interval 540 by a delay interval 560. If more than one noise detection window is utilized, then the noise detection windows may be separated from each other by delay periods. The system senses for noise content during the one or more noise detection intervals 570. If the noise is of sufficient magnitude, then the cardiac signal is determined to be too noisy for accurate cardiac response classification.

In one implementation, the system may determine a magnitude of the cardiac signal during one or more of the classification intervals 530, 540. The cardiac signal magnitude sensed during the one or more classification intervals 530, 540 may be compared to the magnitude of the cardiac signal sensed during the noise interval 570. The ratio of the cardiac signal magnitude in the one or more classification intervals 530, 540 to the cardiac signal magnitude sensed during the noise detection interval 570 provides an estimate of the signal to noise ratio.

The system may incorporate one or more methods for managing fusion and noise. A potentially life threatening situation may arise if noise is erroneously classified as capture or fusion under asystolic conditions. In such a scenario, the system may withhold backup pacing for a number of cycles. The processes of the present invention provide an approach for managing noise to reduce or avoid erroneous classification and/or improper withholding of backup pacing.

During normal pacing, the detection of fusion/pseudofusion beats may indicate less than optimal pacing timing that causes wasted energy due to the generation of unnecessary pace pulses. For example, detection of fusion may trigger scheduling of a hysteresis search routine to determine if lengthening the atrioventricular pacing delay is indicated.

The fusion/noise management processes described herein reduce the risk of noise interfering with cardiac response classification and provide for backup pace delivery when the cardiac response classification is indeterminate or possibly erroneous. Further, the fusion/noise management processes described herein allow the system to discriminate between fusion beats and the presence of noise. The fusion/noise management processes described herein may be implemented if a cardiac response is classified as a fusion beat, if noise is detected, and/or if the cardiac response classification is indeterminate due to noise or other factors.

Some of the fusion/noise management approaches described below are based on the observation that because of overdrive pacing and shortened AV delay, for example, during capture threshold testing, the possibility of fusion is relatively small. For example, less than about 5% of beats are observed to be true fusion beats. Further, the occurrence of multiple consecutive fusion beats, e.g., about five consecutive fusion beats, is extremely rare. Thus, if the system consistently classifies cardiac responses under the noted pacing conditions, as fusion beats, it is likely that the classification is erroneous and that the classified fusion beat is actually noise masquerading as fusion. Fusion/noise management processes according to the present invention involve delivering high energy pacing pulses after detecting fusion or noise.

Figure 6A:
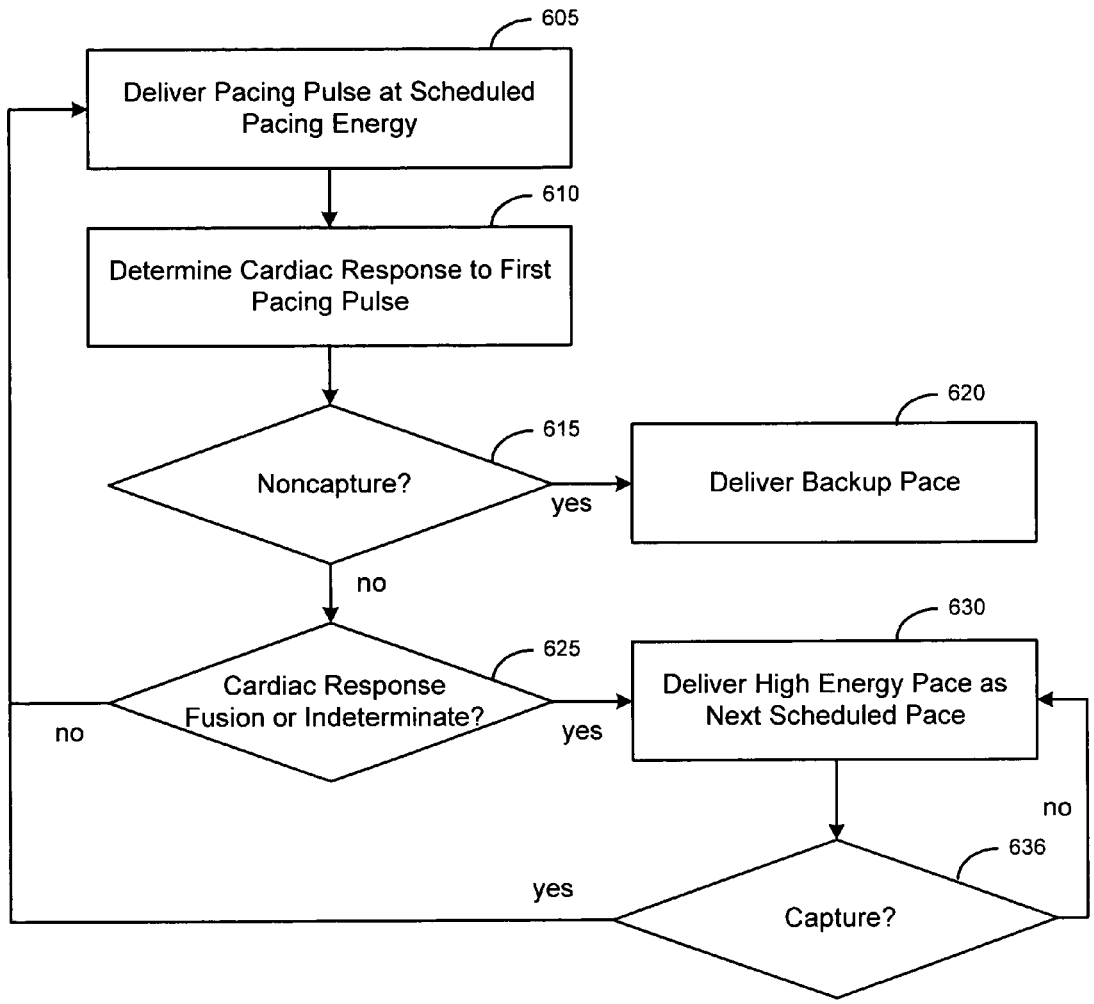
FIG. 6A is a flowchart depicting a fusion/noise management approach in accordance with embodiments of the present invention.

The flowchart of FIG. 6A illustrates a fusion/noise management approach in accordance with embodiments of the present invention. A first pacing pulse is delivered 605 to a heart chamber at a scheduled pacing energy and the cardiac response to the first pacing pulse is determined 610. If the cardiac response is determined to be noncapture 615, then a backup pace may be delivered 620.

If the cardiac response is determined to be 625 fusion or indeterminate due to noise, then the system delivers 630 a high energy pacing pulse, e.g., a pacing pulse having a voltage of 5V, for one or more subsequent pacing cycles. If the cardiac response is not determined to be fusion or indeterminate due to noise 625, then the next pacing pulse is delivered 605 at the scheduled energy level. The system may continue to deliver high energy paces 630 for a number of cycles until a captured-response is detected 636. When capture is detected 636, the system reverts to the pacing 605 at the scheduled pace energy.

By way of example, the processes of the present invention may be used to enhance capture threshold testing to determine the optimal energy for pacing. Determination of the optimal pacing energy may be implemented, for example, by an automatic capture threshold testing procedure executed by an implantable cardiac rhythm management system. Additionally, automatic capture verification may be used to monitor pacing on a beat-by-beat basis. Automatic capture verification may be used to control back up pacing when a pace pulse delivered to the heart fails to evoke a captured response.

These and other applications may be enhanced by employment of the systems and methods of the present invention.

Those skilled in the art will appreciate that reference to a capture threshold procedure indicates a method of determining the capture threshold in one of the left atrium, the right atrium, the left ventricle, and the right ventricle. In such a procedure, the pacemaker, automatically or upon command, initiates a search for the capture threshold of the selected heart chamber or chambers. The capture threshold is defined as the lowest pacing energy that consistently produces a contraction of the heart chamber.

In one example of an automatic capture threshold procedure, the pacemaker delivers a sequence of pacing pulses to the heart and detects the cardiac responses to the pace pulses. The energy of the pacing pulses may be decreased in discrete steps until a predetermined number of loss-of-capture events occur. After the predetermined number of loss-of-capture events occur, the pacemaker may increase the stimulation energy in discrete steps until a predetermined number of capture events occur to confirm the capture threshold. A capture threshold test may be performed using cardiac response classification methods of the present invention.

Other procedures for implementing capture threshold testing may be utilized. In one example, the pacing energy may be increased in discrete steps until capture is detected. In another example, the pacing energy may be adjusted according to a binomial search pattern.

Automatic capture threshold determination is distinguishable from automatic capture detection, a procedure that may occur on a beat-by-beat basis during pacing. Automatic capture detection verifies that a delivered pace pulse results in a captured response. When a captured response is not detected following a pace pulse, the pacemaker may deliver a back up safety pace to ensure consistent pacing. The back up pace may be delivered, for example, about 90-110 ms after the initial pace pulse. If a predetermined number of pace pulses delivered during normal pacing do not produce a captured response, the pacemaker may initiate a capture threshold test to determine the capture threshold. Automatic capture detection and back up pacing may be enhanced using the noise discrimination and fusion/noise management processes of the present invention.

Figure 6B:
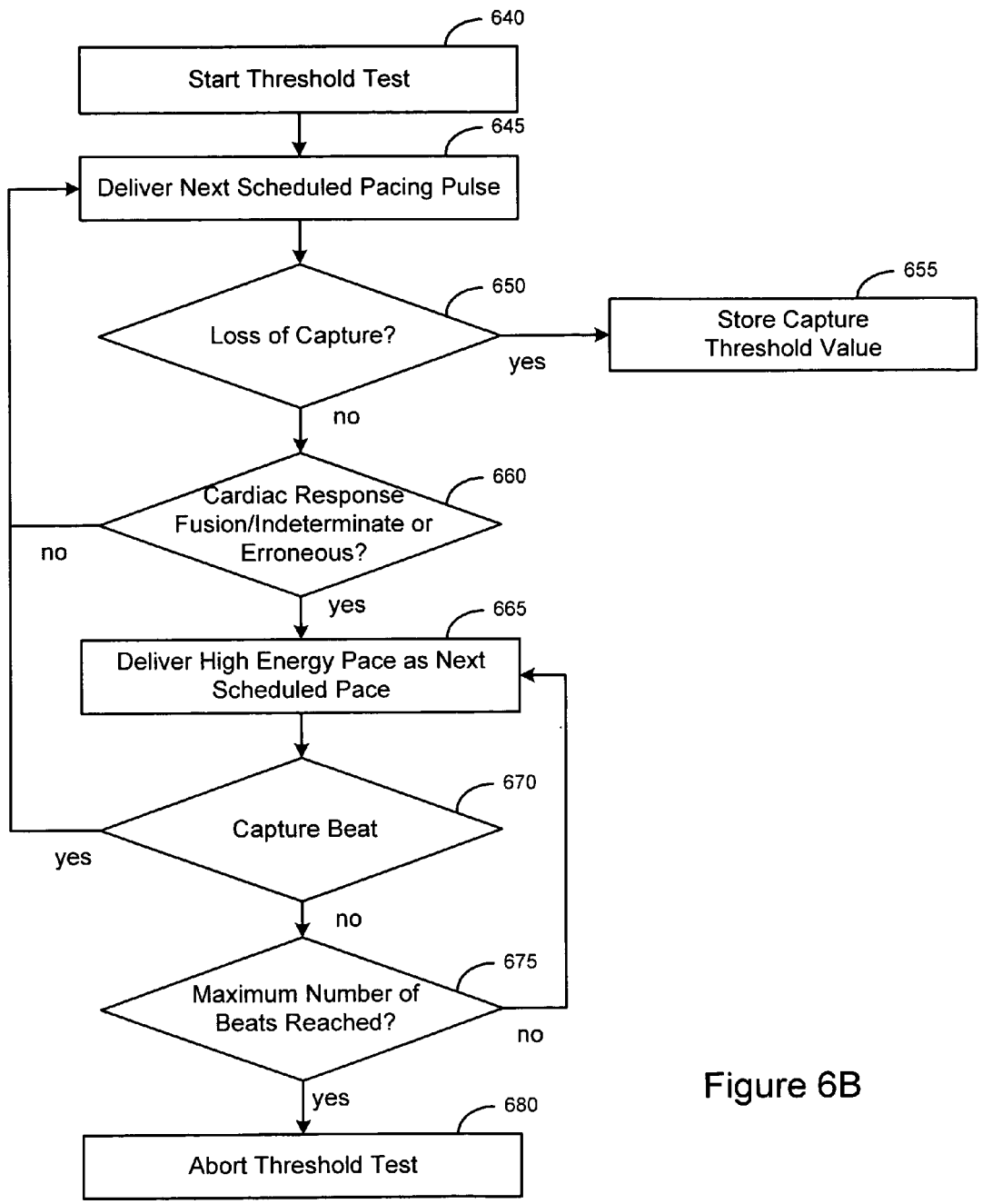
FIG. 6B is a flowchart illustrating an approach that may be used for fusion/noise management during a capture threshold test.

The flowchart of FIG. 6B illustrates an approach that may be used for fusion/noise management during a capture threshold test. After initiation of the capture threshold test 640, one or more pacing pulses are delivered at decreasing energy levels to determine the capture threshold. Following delivery of a pacing pulse 645, the system determines if loss of capture has occurred. Loss of capture may be declared for example when x out of y beats are determined to be noncaptured beats. If loss of capture is declared 650, then the capture threshold energy identified by the test is stored 655 and the test ends.

If loss of capture is not detected 650, then the system determines 660 if the pacing pulse resulted in a fusion beat or an indeterminate response or if the cardiac response is possibly erroneous. If so, the next scheduled pace is delivered 665 at a high energy level, e.g., a voltage level of 5V.

The system determines the cardiac response to the high energy pace. If the cardiac response to the high energy pace is a captured response beat 670, then it is likely that the previous beat was truly a fusion response. The threshold test is resumed and the next pace is delivered 645 at the scheduled pacing energy.

If the cardiac response to the high energy pace is not capture 670, i.e., remains a fusion/indeterminate response or if the cardiac response classification is possibly erroneous due to noise, then one or more additional high energy paces are delivered 665 so long as a maximum number of high energy beats is not exceeded 675. If the maximum number of high energy paces, e.g., about 4 beats, is delivered without producing a captured response, the sensing channel is likely noisy and the threshold test is aborted 680.

Figure 7A:
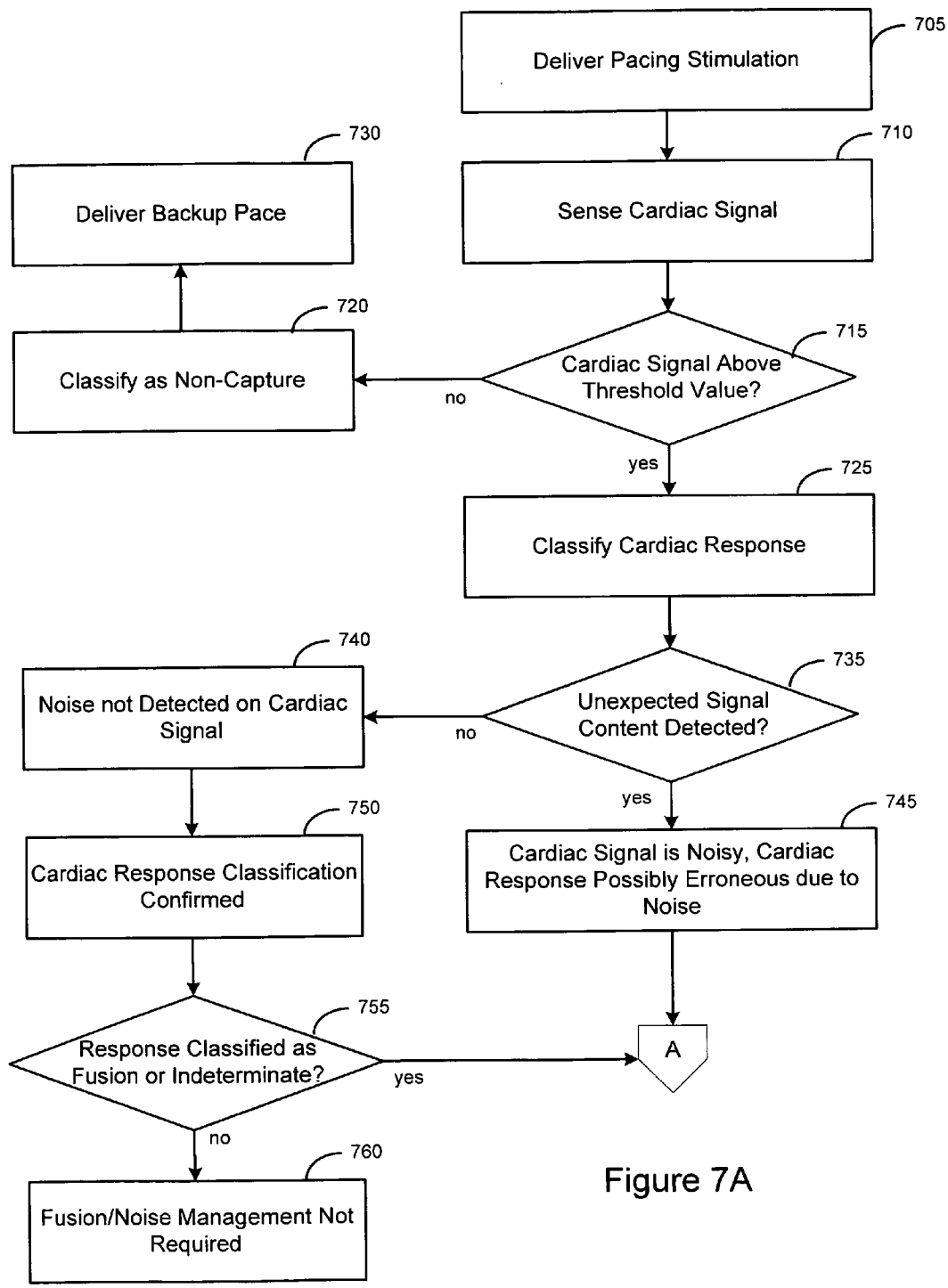
FIGS. 7A and 7B illustrate a method of noise detection and fusion/noise management in accordance with embodiments of the invention.
Figure 7B:
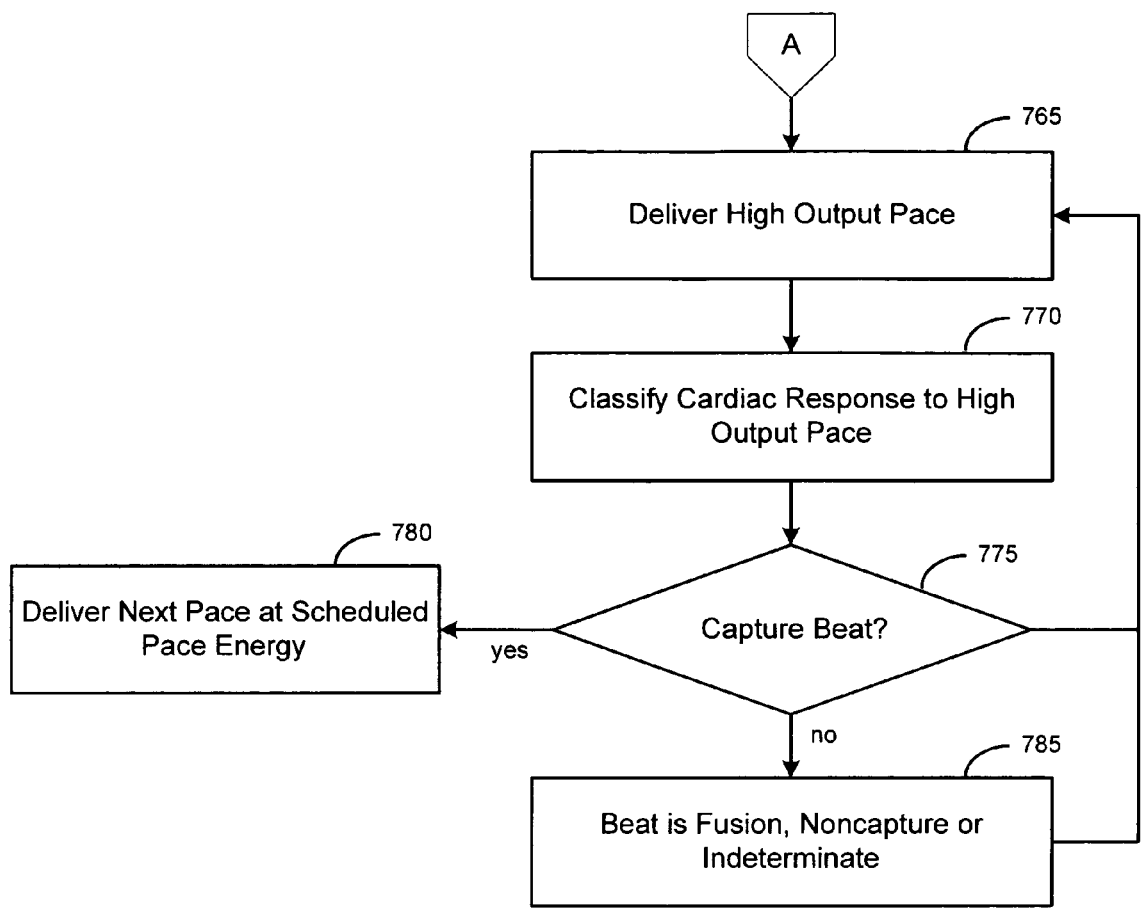

In accordance with various embodiments, the noise detection techniques previously described may be combined with fusion/noise management processes. The flowchart of FIGS. 7A and 7B illustrates a method for detecting noise and for managing fusion, indeterminate, and/or noisy beats in accordance with embodiments of the invention. For example, a beat may be classified as a fusion beat if the one or more peaks of the cardiac signal are detected in one or more appropriate classification windows. Noise may be detected on the cardiac signal, in which case the cardiac response classification is possibly erroneous. If noise is not detected on the cardiac signal, the cardiac response may be indeterminate if one or more signal peaks are not detected in the cardiac response classification windows. If fusion is detected, if the cardiac response classification is indeterminate, or if the cardiac response classification is possibly erroneous due to noise, the fusion/noise management process is implemented.

Following delivery of a pacing pulse 705, the system senses for 710 expected and unexpected peaks in the cardiac signal associated with the pacing pulse. If the magnitude of the cardiac signal remains below 715 a threshold value, then the cardiac response is classified 720 as a noncaptured response and a backup pacing pulse may be delivered 730.

If the cardiac signal magnitude exceeds 715 the threshold level, the system classifies 725 the cardiac pacing response. The cardiac pacing response may be classified, for example, as capture, fusion, or noncapture with intrinsic activity based on cardiac signal peaks detected in cardiac response classification windows. Further, the cardiac response may be classified as indeterminate if the system cannot determine the cardiac response, e.g., if the peaks of the cardiac signals fall outside the classification windows. The signal checks to see if unexpected signal content is detected 735. If unexpected signal content is not detected 735, then the cardiac signal is not noisy 740. The cardiac response classification made at block 725 is confirmed 750. If the cardiac response is fusion or indeterminate, then a fusion/noise management process illustrated by the flowchart of FIG. 7B is performed. If the cardiac response is not fusion or an indeterminate response 755, fusion/noise management is not required 760.

If unexpected signal content is detected 735, then the cardiac signal is noisy and the cardiac response classification is possibly erroneous 745 due to noise. The fusion/noise management process illustrated by the flowchart of FIG. 7B is performed.

If the cardiac response is fusion or an indeterminate response 755 or if the cardiac response classification is possibly erroneous 745 due to noise, then a high energy pace is delivered 765 (FIG. 7B). The system classifies 770 the cardiac response to the high energy pace. If the cardiac response to the high energy pace is a captured response 775, then the next pace is delivered 780 at the previously scheduled energy level and the process repeats 705. If the cardiac response to the high energy pace is not capture 775, then the beat is fusion, noncapture or indeterminate 785, and one or more additional high energy paces are delivered 765. Additional high energy paces may be delivered, for example, until a maximum number of high energy paces have been delivered or until a captured beat is detected.

The embodiments of the present system illustrated herein are generally described as being implemented in an implantable cardiac defibrillator (ICD) that may operate in numerous pacing modes known in the art. Various types of single and multiple chamber implantable cardiac defibrillators are known in the art and may be used in connection with the cardiac response classification methods of the present invention. The methods of the present invention may also be implemented in a variety of implantable or patient-external cardiac rhythm management devices, including single and multi chamber pacemakers, defibrillators, cardioverters, bi-ventricular pacemakers, cardiac resynchronizers, and cardiac monitoring systems, for example.

Although the present system is described in conjunction with an implantable cardiac defibrillator having a microprocessor-based architecture, it will be understood that the implantable cardiac defibrillator (or other device) may be implemented in any logic-based integrated circuit architecture, if desired.

Figure 8:
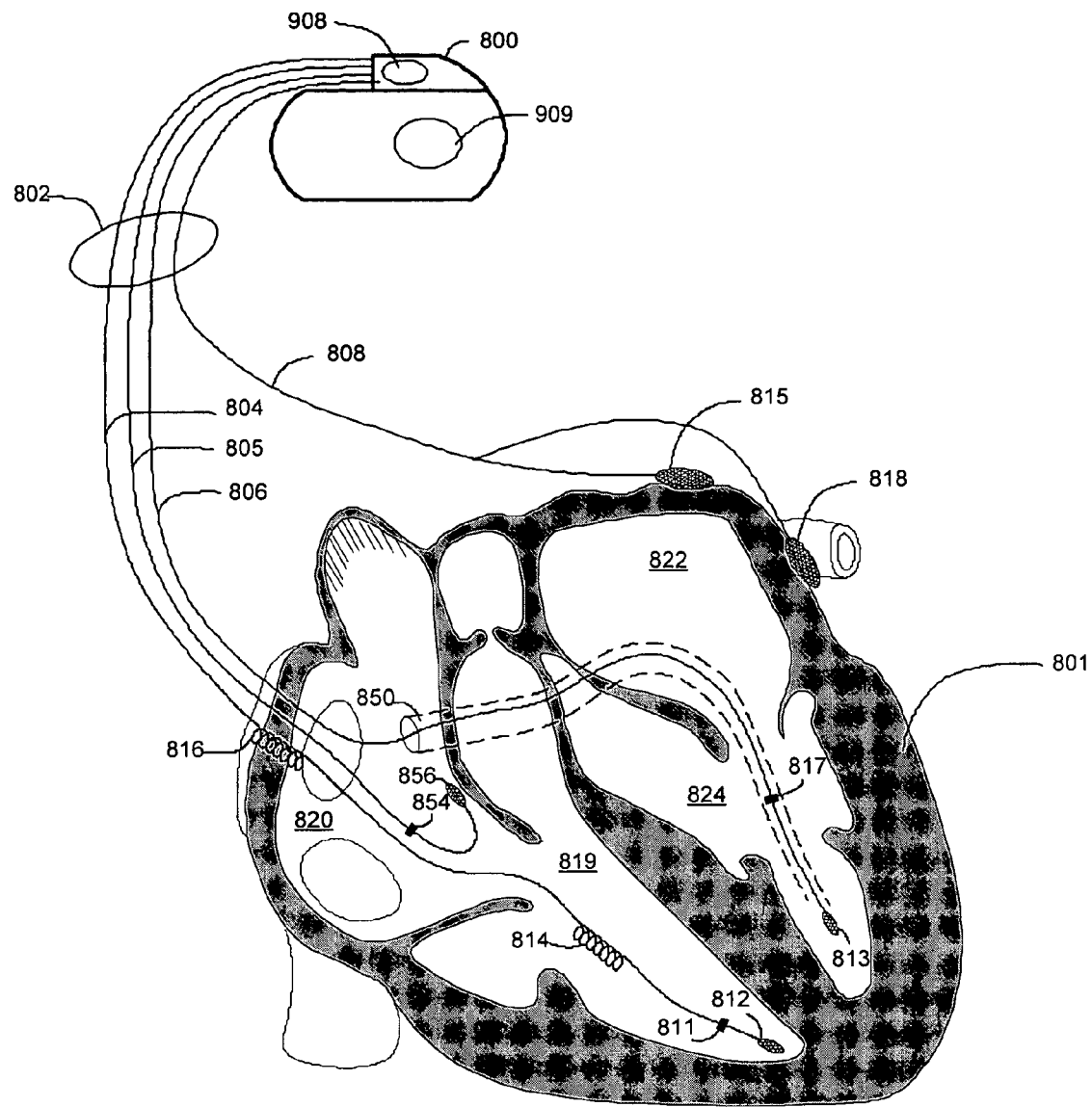
FIG. 8 is a partial view of one embodiment of an implantable medical device in accordance with embodiments of the invention.

Referring now to FIG. 8 of the drawings, there is shown a cardiac rhythm management system that may be used to implement noise discrimination and management methods of the present invention. The cardiac rhythm management system in FIG. 8 includes an ICD 800 electrically and physically coupled to a lead system 802. The housing and/or header of the ICD 800 may incorporate one or more electrodes 908, 909 used to provide electrical stimulation energy to the heart and to sense cardiac electrical activity. The ICD 800 may utilize all or a portion of the ICD housing as a can electrode 909. The ICD 800 may include an indifferent electrode positioned, for example, on the header or the housing of the ICD 800. If the ICD 800 includes both a can electrode 909 and an indifferent electrode 908, the electrodes 908, 909 typically are electrically isolated from each other.

The lead system 802 is used to detect electric cardiac signals produced by the heart 801 and to provide electrical energy to the heart 801 under certain predetermined conditions to treat cardiac arrhythmias. The lead system 802 may include one or more electrodes used for pacing, sensing, and/or defibrillation. In the embodiment shown in FIG. 8, the lead system 802 includes an intracardiac right ventricular (RV) lead system 804, an intracardiac right atrial (RA) lead system 805, an intracardiac left ventricular (LV) lead system 806, and an extracardiac left atrial (LA) lead system 808. The lead system 802 of FIG. 8 illustrates one embodiment that may be used in connection with the cardiac response classification methodologies described herein. Other leads and/or electrodes may additionally or alternatively be used.

The lead system 802 may include intracardiac leads 804, 805, 806 implanted in a human body with portions of the intracardiac leads 804, 805, 806 inserted into a heart 801. The intracardiac leads 804, 805, 806 include various electrodes positionable within the heart for sensing electrical activity of the heart and for delivering electrical stimulation energy to the heart, for example, pacing pulses and/or defibrillation shocks to treat various arrhythmias of the heart.

As illustrated in FIG. 8, the lead system 802 may include one or more extracardiac leads 808 having electrodes, e.g., epicardial electrodes, positioned at locations outside the heart for sensing and pacing one or more heart chambers.

The right ventricular lead system 804 illustrated in FIG. 8 includes an SVC-coil 816, an RV-coil 814, an RV-ring electrode 811, and an RV-tip electrode 812. The right ventricular lead system 804 extends through the right atrium 820 and into the right ventricle 819. In particular, the RV-tip electrode 812, RV-ring electrode 811, and RV-coil electrode 814 are positioned at appropriate locations within the right ventricle 819 for sensing and delivering electrical stimulation pulses to the heart. The SVC-coil 816 is positioned at an appropriate location within the right atrium chamber 820 of the heart 801 or a major vein leading to the right atrial chamber 820 of the heart 801.

In one configuration, the RV-tip electrode 812 referenced to the can electrode 909 may be used to implement unipolar pacing and/or sensing in the right ventricle 819. Bipolar pacing and/or sensing in the right ventricle may be implemented using the RV-tip 812 and RV-ring 811 electrodes. In yet another configuration, the RV-ring 811 electrode may optionally be omitted, and bipolar pacing and/or sensing may be accomplished using the RV-tip electrode 812 and the RV-coil 814, for example. The right ventricular lead system 804 may be configured as an integrated bipolar pace/shock lead. The RV-coil 814 and the SVC-coil 816 are defibrillation electrodes.

The left ventricular lead 806 includes an LV distal electrode 813 and an LV proximal electrode 817 located at appropriate locations in or about the left ventricle 824 for pacing and/or sensing the left ventricle 824. The left ventricular lead 806 may be guided into the right atrium 820 of the heart via the superior vena cava. From the right atrium 820, the left ventricular lead 806 may be deployed into the coronary sinus ostium, the opening of the coronary sinus 850. The lead 806 may be guided through the coronary sinus 850 to a coronary vein of the left ventricle 824. This vein is used as an access pathway for leads to reach the surfaces of the left ventricle 824 which are not directly accessible from the right side of the heart. Lead placement for the left ventricular lead 806 may be achieved via subclavian vein access and a preformed guiding catheter for insertion of the LV electrodes 813, 817 adjacent to the left ventricle.

Unipolar pacing and/or sensing in the left ventricle may be implemented, for example, using the LV distal electrode referenced to the can electrode 909. The LV distal electrode 813 and the LV proximal electrode 817 may be used together as bipolar sense and/or pace electrodes for the left ventricle. The left ventricular lead 806 and the right ventricular lead 804, in conjunction with the ICD 800, may be used to provide cardiac resynchronization therapy such that the ventricles of the heart are paced substantially simultaneously, or in phased sequence, to provide enhanced cardiac pumping efficiency for patients suffering from chronic heart failure.

The right atrial lead 805 includes an RA-tip electrode 856 and an RA-ring electrode 854 positioned at appropriate locations in the right atrium 820 for sensing and pacing the right atrium 820. In one configuration, the RA-tip 856 referenced to the can electrode 909, for example, may be used to provide unipolar pacing and/or sensing in the right atrium 820. In another configuration, the RA-tip electrode 856 and the RA-ring electrode 854 may be used to effect bipolar pacing and/or sensing.

FIG. 8 illustrates one embodiment of a left atrial lead system 808. In this example, the left atrial lead 808 is implemented as an extracardiac lead with LA distal 818 and LA proximal 815 electrodes positioned at appropriate locations outside the heart 801 for sensing and pacing the left atrium 822. Unipolar pacing and/or sensing of the left atrium may be accomplished, for example, using the LA distal electrode 818 to the can 909 pacing vector. The LA proximal 815 and LA distal 818 electrodes may be used together to implement bipolar pacing and/or sensing of the left atrium 822.

Figure 9A:
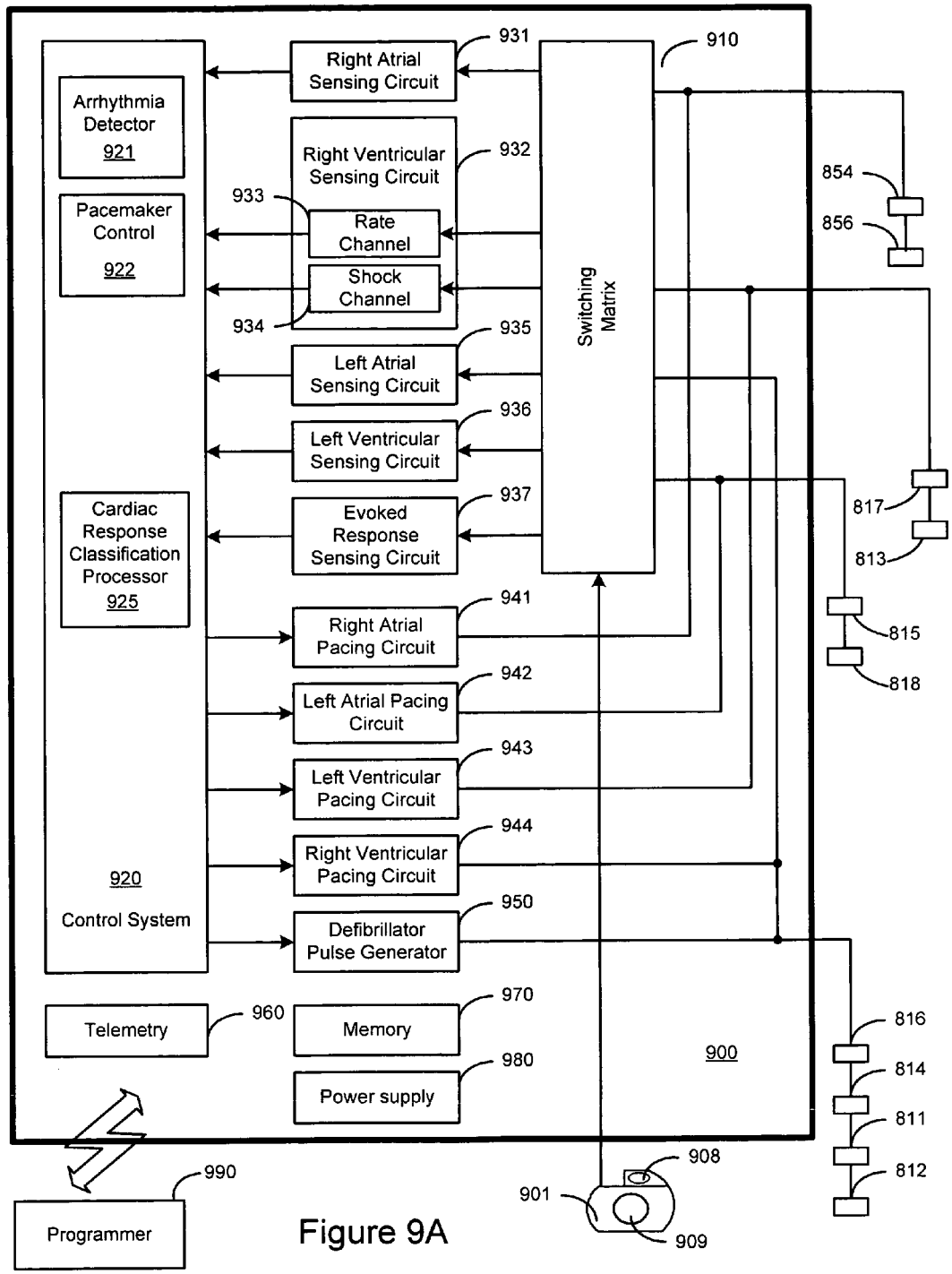
FIG. 9A is a block diagram of an implantable medical device that may be used to classify a cardiac response to pacing in accordance with embodiments of the invention.

Referring now to FIG. 9A, there is shown an embodiment of a cardiac defibrillator 900 suitable for implementing a noise discrimination and fusion/noise management methodology of the present invention. FIG. 9A shows a cardiac defibrillator divided into functional blocks. It is understood by those skilled in the art that there exist many possible configurations in which these functional blocks can be arranged. The example depicted in FIG. 9A is one possible functional arrangement. Other arrangements are also possible. For example, more, fewer, or different functional blocks may be used to describe a cardiac defibrillator suitable for implementing the methodologies for classifying the cardiac response to pacing with noise discrimination and fusion/noise management of the present invention. In addition, although the cardiac defibrillator 900 depicted in FIG. 9A contemplates the use of a programmable microprocessor-based logic circuit, other circuit implementations may be utilized.

The cardiac defibrillator 900 depicted in FIG. 9A includes circuitry for receiving cardiac signals from a heart and delivering electrical stimulation energy to the heart in the form of pacing pulses or defibrillation shocks. In one embodiment, the circuitry of the cardiac defibrillator 900 is encased and hermetically sealed in a housing 901 suitable for implanting in a human body. Power to the cardiac defibrillator 900 is supplied by an electrochemical battery 980. A connector block (not shown) is attached to the housing 901 of the cardiac defibrillator 900 to allow for the physical and electrical attachment of the lead system conductors to the circuitry of the cardiac defibrillator 900.

The cardiac defibrillator 900 may be a programmable microprocessor-based system, including a control system 920 and a memory 970. The memory 970 may store parameters for various pacing, defibrillation, and sensing modes, along with other parameters. Further, the memory 970 may store data indicative of cardiac signals received by other components of the cardiac defibrillator 900. The memory 970 may be used, for example, for storing historical EGM and therapy data. The historical data storage may include, for example, data obtained from long term patient monitoring used for trending or other diagnostic purposes. Historical data, as well as other information, may be transmitted to an external programmer unit 990 as needed or desired.

The control system 920 and memory 970 may cooperate with other components of the cardiac defibrillator 900 to control the operations of the cardiac defibrillator 900. The control system depicted in FIG. 9A incorporates a cardiac response classification processor 925 for classifying cardiac responses to pacing stimulation and including noise discrimination and fusion/noise management circuitry in accordance with various embodiments of the present invention. The control system 920 may include additional functional components including a pacemaker control circuit 922, an arrhythmia detector 921, and a template processor for cardiac signal morphology analysis, along with other components for controlling the operations of the cardiac defibrillator 900.

Telemetry circuitry 960 may be implemented to provide communications between the cardiac defibrillator 900 and an external programmer unit 990. In one embodiment, the telemetry circuitry 960 and the programmer unit 990 communicate using a wire loop antenna and a radio frequency telemetric link, as is known in the art, to receive and transmit signals and data between the programmer unit 990 and the telemetry circuitry 960. In this manner, programming commands and other information may be transferred to the control system 920 of the cardiac defibrillator 900 from the programmer unit 990 during and after implant. In addition, stored cardiac data pertaining to capture threshold, capture detection, and/or cardiac response classification, for example, along with other data, may be transferred to the programmer unit 990 from the cardiac defibrillator 900.

In the embodiment of the cardiac defibrillator 900 illustrated in FIG. 9A, electrodes RA-tip 856, RA-ring 854, RV-tip 812, RV-ring 811, RV-coil 814, SVC-coil 816, LV distal electrode 813, LV proximal electrode 817, LA distal electrode 818, LA proximal electrode 815, indifferent electrode 908, and can electrode 909 are coupled through a switch matrix 910 to sensing circuits 931-937.

A right atrial sensing circuit 931 serves to detect and amplify electrical signals from the right atrium of the heart. Bipolar sensing in the right atrium may be implemented, for example, by sensing voltages developed between the RA-tip 856 and the RA-ring 854. Unipolar sensing may be implemented, for example, by sensing voltages developed between the RA-tip 856 and the can electrode 909. Outputs from the right atrial sensing circuit are coupled to the control system 920.

A right ventricular sensing circuit 932 serves to detect and amplify electrical signals from the right ventricle of the heart. The right ventricular sensing circuit 932 may include, for example, a right ventricular rate channel 933 and a right ventricular shock channel 934. Right ventricular cardiac signals sensed through use of the RV-tip 812 electrode are right ventricular near-field signals and are denoted RV rate channel signals. A bipolar RV rate channel signal may be sensed as a voltage developed between the RV-tip 812 and the RV-ring 811. Alternatively, bipolar sensing in the right ventricle may be implemented using the RV-tip electrode 812 and the RV-coil 814. Unipolar rate channel sensing in the right ventricle may be implemented, for example, by sensing voltages developed between the RV-tip 812 and the can electrode 909.

Right ventricular cardiac signals sensed through use of the RV-coil electrode 814 are far-field signals, also referred to as RV morphology or RV shock channel signals. More particularly, a right ventricular shock channel signal may be detected as a voltage developed between the RV-coil 814 and the SVC-coil 816. A right ventricular shock channel signal may also be detected as a voltage developed between the RV-coil 814 and the can electrode 909. In another configuration, the can electrode 909 and the SVC-coil electrode 816 may be electrically shorted and an RV shock channel signal may be detected as the voltage developed between the RV-coil 814 and the can electrode 909/SVC-coil 816 combination.

Outputs from the right ventricular sensing circuit 932 are coupled to the control system 920. In one embodiment of the invention, rate channel signals and shock channel signals may be used to develop morphology templates for analyzing cardiac signals. In this embodiment, rate channel signals and shock channel signals may be transferred from the right ventricular sensing circuit 932 to the control system 920 and to a template processor where the morphological characteristics of a cardiac signal are analyzed for arrhythmia detection.

Left atrial cardiac signals may be sensed through the use of one or more left atrial electrodes 815, 818, which may be configured as epicardial electrodes. A left atrial sensing circuit 935 serves to detect and amplify electrical signals from the left atrium of the heart. Bipolar sensing and/or pacing in the left atrium may be implemented, for example, using the LA distal electrode 818 and the LA proximal electrode 815. Unipolar sensing and/or pacing of the left atrium may be accomplished, for example, using the LA distal electrode 818 to can vector 909 or the LA proximal electrode 815 to can vector 909.

A left ventricular sensing circuit 936 serves to detect and amplify electrical signals from the left ventricle of the heart. Bipolar sensing in the left ventricle may be implemented, for example, by sensing voltages developed between the LV distal electrode 813 and the LV proximal electrode 817. Unipolar sensing may be implemented, for example, by sensing voltages developed between the LV distal electrode 813 or the LV proximal electrode 817 to the can electrode 909.

Optionally, an LV coil electrode (not shown) may be inserted into the patient's cardiac vasculature, e.g., the coronary sinus, adjacent to the left heart. Signals detected using combinations of the LV electrodes 813, 817, the LV coil electrode (not shown), and/or the can electrode 909 may be sensed and amplified by the left ventricular sensing circuitry 936. The output of the left ventricular sensing circuit 936 is coupled to the control system 920.

The outputs of the switching matrix 910 may be operated to couple selected combinations of electrodes 811, 812, 813, 814, 815, 816, 817, 818, 856, 854 to an evoked response sensing circuit 937. The evoked response sensing circuit 937 serves to sense and amplify voltages developed using various combinations of electrodes for cardiac response classification in accordance with embodiments of the invention.

In the embodiments described below, various combinations of pacing and sensing electrodes may be utilized in connection with pacing and sensing the cardiac signal following the pace pulse to classify the cardiac response to the pacing pulse. For example, in some embodiments, a first electrode combination is used for pacing a heart chamber and a second electrode combination is used to sense the cardiac signal following pacing. In other embodiments, the same electrode combination is used for pacing and sensing.

Sensing the cardiac signal following a pacing pulse using the same electrode combination for both pacing and sensing may yield a sensed cardiac signal including a pacing artifact component associated with residual post pace polarization at the electrode-tissue interface. The pacing artifact component may be superimposed on a smaller signal indicative of the cardiac response to the pacing pulse, i.e., the evoked response. The pacing output circuitry may include a coupling capacitor to block DC components from the heart and to condition the pacing stimulus pulse. A relatively large coupling capacitor may cause a larger pacing artifact that decays exponentially over a relatively large period of time.

The presence of a large pacing artifact signal may complicate the classification of the cardiac response to pacing. Various embodiments of the invention are directed to methods involving detection of a cardiac signal following pacing and canceling the pacing artifact from the detected signal. Classification of the cardiac response to pacing may be implemented using the pacing artifact cancelled signal. Cancellation of the pacing artifact in cardiac response classification is particularly important when the same or similar electrode combinations are used both for delivering pacing pulses and for sensing the cardiac signals following the delivery of the pacing pulses. Cancellation of the pacing artifact may also be used when a first electrode combination is used for pacing the heart chamber and a different electrode combination is used to sense the subsequent cardiac response. Methods and systems for pacing artifact cancellation are described in commonly owned U.S. patent application Ser. No. 10/335,534, filed Dec. 31, 2002, now U.S. Pat. No. 7,162,301, which is incorporated by reference herein in its entirety.

In various embodiments described herein, a first electrode combination may be used for pacing the heart chamber and a second electrode combination used for sensing the cardiac signals following the pace for cardiac response classification. If different electrode combinations are used for pacing and sensing, a temporal separation between the cardiac response signal, e.g., the evoked response, and the pacing artifact may facilitate classification of the cardiac response to pacing. The temporal separation occurs due to the propagation delay of the depolarization wavefront initiated at the pacing electrode and traveling to a sensing electrode that is physically spaced apart from the pacing electrode. The temporal separation of the cardiac response signal and the pacing artifact may be sufficient to obviate cancellation of the pacing artifact. Use of different electrodes for pacing and sensing in connection with capture verification is described in commonly owned U.S. Pat. No. 6,128,535 which is incorporated herein by reference.

The pacemaker control circuit 922, in combination with pacing circuitry for the left atrium, right atrium, left ventricle, and right ventricle 941, 942, 943, 944, may be implemented to selectively generate and deliver pacing pulses to the heart using various electrode combinations. The pacing electrode combinations may be used to effect bipolar or unipolar pacing of the heart chambers as described above As described above, bipolar or unipolar pacing pulses may be delivered to a heart chamber using one of the pacing vectors as described above. The electrical signal following the delivery of the pacing pulses may be sensed through various sensing vectors coupled through the switch matrix 910 to the evoked response sensing circuit 937 and used to classify the cardiac response to pacing.

In one example, the cardiac signal following the pacing pulse may be sensed using the same vector as was used for delivery of the pacing pulse. In this scenario, the pacing artifact may be canceled from the sensed cardiac signal using the pacing artifact cancellation techniques described below. Following cancellation of the pacing artifact, one or more time intervals and cardiac response classification windows may be defined following the pacing pulse and used to classify the cardiac response to pacing. The cardiac response may be classified as one of a captured response, a non-captured response, a non-captured response with intrinsic activation, and a fusion/pseudofusion beat, for example. As described above, noise may cause the system to be unable to accurately classify the cardiac response. In this scenario, the cardiac response to the pacing pulse is indeterminate.

In another example, the vector used to sense the cardiac signal following the pacing pulse may be different from the vector that was used to deliver the pacing pulse. The sensing vector may be selected to minimize the pacing artifact. Cancellation of the pacing artifact may not be necessary if the pacing artifact is sufficiently minimized using this technique.

In various embodiments, the pacing vector may be a near-field vector and the sensing vector may be a far-field vector. In an example of right ventricular pacing and cardiac response sensing, the pacing vector may be the rate channel vector and the sensing vector may be the shock channel vector.

Subcutaneous electrodes may provide additional sensing vectors useable for cardiac response classification. In one implementation, a cardiac rhythm management system may involve a hybrid system including an intracardiac device configured to pace the heart and an extracardiac device, e.g., a subcutaneous defibrillator, configured to perform functions other than pacing. The extracardiac device may be employed to detect and classify the cardiac response to pacing based on signals sensed using subcutaneous electrode arrays. The extracardiac and intracardiac devices may operate cooperatively with communication between the devices occurring over a wireless link, for example. Examples of subcutaneous electrode systems and devices are described in commonly owned U.S. Patent Publication No. 2004/0230229, and U.S. Patent Publication No. 2004/0230229, which are incorporated herein by reference in their respective entireties.

For right ventricular pacing, bipolar pacing may be delivered using the RV-tip electrode 812 and the RV-ring electrode 811. Unipolar pacing may be delivered using the RV-tip 812 to can 909 vector. The preferred sensing electrode combinations for cardiac response classification following RV pacing include RV-coil 814 to SVC-coil 816 tied to the can electrode 909, RV-coil 814 to can electrode 909, and, if the system includes a left ventricular lead, LV distal electrode 813 to LV proximal electrode 817.

In an example of left ventricular pacing, bipolar pacing pulses may be delivered to the left ventricle between the LV distal electrode 813 and the LV proximal electrode 817. In another example, unipolar pacing pulses may be delivered to the left ventricle, for example, between the LV distal electrode 813 and the can 909. The cardiac signal following the delivery of the pacing pulses may preferably be sensed using the LV proximal electrode 817 and the can 909.

In an example of right atrial pacing, bipolar pacing pulses may be delivered to the right atrium between the RA-tip electrode 856 and the RA-ring electrode 854. In another example, unipolar pacing pulses may be delivered to the right atrium, for example, between the RA-tip electrode 856 and the can electrode 909. For unipolar right atrial pacing, the preferred electrode combination for sensing cardiac signals following pacing for cardiac response classification comprises the RA-ring 854 to indifferent electrode.

In an example of left atrial pacing, bipolar pacing pulses may be delivered to the left atrium between the LA distal electrode 818 and the LA proximal electrode 815. In another example, unipolar pacing pulses may be delivered to the left atrium, for example, between the LA distal electrode 818 and the can electrode 909. The cardiac signal following the delivery of the pacing pulses and used for cardiac response classification may preferably be sensed using the RA-tip 856 to RA-ring 854 vector.

In one embodiment of the invention, a switching matrix 910 is coupled to the RA-tip 856, RA-ring 854, RV-tip 812, RV-coil 814, LV distal electrode 813, LV proximal electrode 817, SVC coil 816, LA distal electrode 818, LA proximal electrode 815, indifferent, and can 909 electrodes. The switching matrix 910 may be arranged to provide connections to various configurations of pacing and defibrillation electrodes. The outputs of the switching matrix 910 are coupled to an evoked response (ER) sensing circuit 937 that serves to sense and amplify cardiac signals detected between the selected combinations of electrodes. The detected signals are coupled through the ER amplifier 937 to a cardiac response classification processor 925. The cardiac response classification processor 925 includes circuitry configured to classify a cardiac response to a pacing stimulation, including, for example, classifying a captured response, a non-captured response, an intrinsic beat added to a non-captured response, and a fusion/pseudofusion response, in accordance with the invention. If noise prevents accurate classification of the cardiac response, the cardiac response is indeterminate.

Figure 9B:
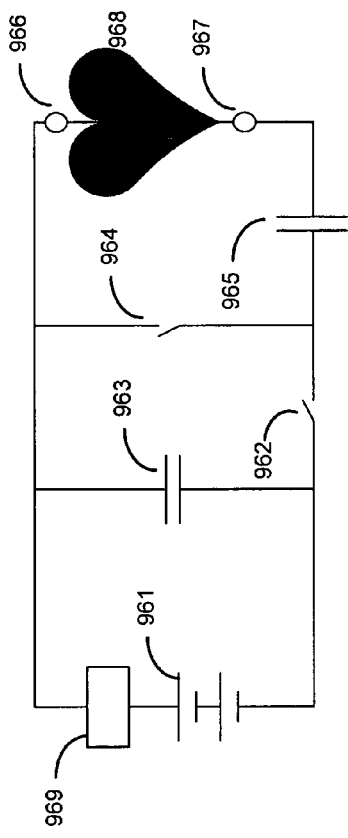
FIG. 9B is a schematic diagram of a circuit that may be used to generate pacing stimulations in accordance with embodiments of the invention.
Figure 9C:
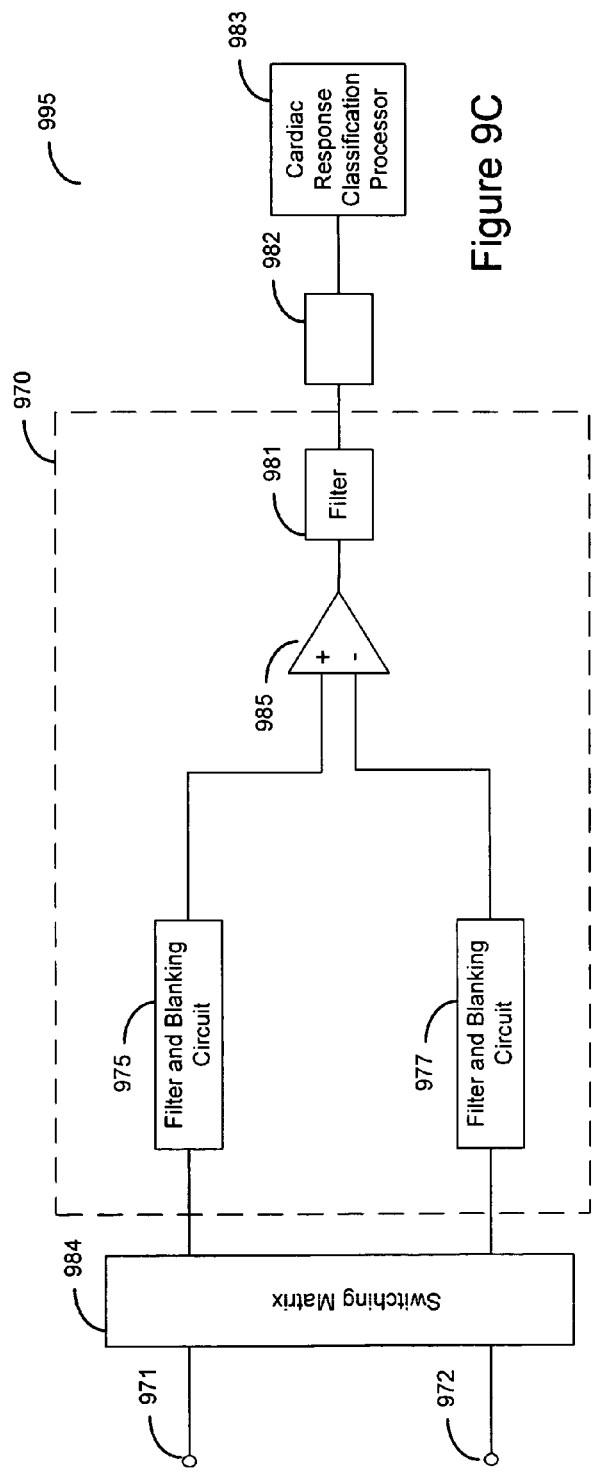
FIG. 9C is a schematic diagram of a circuit that may be used to sense a cardiac signal following the delivery of a pacing stimulation and to classify the cardiac response to the pacing stimulation according to embodiments of the invention.

FIGS. 9B and 9C illustrate more detailed examples of pacing and sensing circuitry, respectively, that may be used for cardiac pace/sense channels of a pacemaker in accordance with embodiments of the invention. It will be appreciated that the example pacing and sensing circuits illustrated in FIGS. 9B and 9C may be arranged to achieve the pacing and sensing vectors described above.

In example embodiments of the invention, the pacing circuit of FIG. 9B includes a power supply or battery 961, a first switch 962, a second switch 964, a pacing charge storage capacitor 963, coupling capacitor 965, and a pacing capacitor charging circuit 969, all of which are cooperatively operable under the direction of a controller of known suitable construction. The power supply or battery 961 is preferably the battery provided to power the pacemaker and may comprise any number of commercially available batteries suitable for pacing applications. The switches 962, 964 may be implemented using any number of conventionally available switches. The pacing capacitor charging circuit 969 includes circuitry to regulate the voltage across the pacing charge storage capacitor 963.

The pacing charge storage capacitor 963 may also comprise any number of conventional storage capacitors that can be used to develop a sufficient pacing charge for stimulating the heart. The primary function of the coupling capacitor 965 is to attenuate the polarization voltage or "afterpotential" which results from pacing and additionally block any DC signals from reaching the heart 968 during pacing. The coupling capacitor 965 may have a capacitance, for example, in the range of about 9 microfarads to about 22 microfarads. Energy stored in the pacing charge storage capacitor 963 may be delivered to the heart 968 using various combinations of cardiac electrodes 966, 967, as described above.

FIG. 9C illustrates a block diagram of the circuit 995 that may be used to sense cardiac signals following the delivery of a pacing stimulation and classify the cardiac response to the pacing stimulation according to embodiments of the invention. A switch matrix 984 is used to couple the cardiac electrodes 971, 972 in various combinations discussed above to the sensing portion 970 of the cardiac response classification circuit 995. The sensing portion 970 includes filtering and blanking circuitry 975, 977, sense amplifier 985, band pass filter 981, and window generation and signal characteristic detector 982. The window generation and signal characteristic detector 982 is coupled to a cardiac response classification processor 983.

A control system, e.g., the control system 920 depicted in FIG. 9A, is operatively coupled to components of the cardiac response classification circuit 995 and controls the operation of the cardiac response classification circuit 995, including the filtering and blanking circuits 975, 977. Following a blanking period of sufficient duration following delivery of the pacing stimulation, the blanking circuitry 975, 977 operates to allow detection of a cardiac signal responsive to the pacing stimulation. The cardiac signal is filtered, amplified, and converted from analog to digital form. The digitized signal is communicated to the cardiac response classification processor 983, which operates in cooperation with other components of the control system 920 (FIG. 9A) to classify cardiac responses to pacing according to embodiments of the invention.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method for detecting cardiac signal noise during capture verification, comprising:
   delivering a pacing pulse to a heart chamber;
   sensing a cardiac signal associated with the pacing pulse;
   classifying a cardiac response to the pacing pulse based on the sensed cardiac signal, the cardiac response classification being one of a plurality of expected cardiac responses including capture and intrinsic activation;
   sensing for unexpected signal content in the cardiac signal, the unexpected signal content being inconsistent with one or more of capture and intrinsic activation and comprising one or more of unexpected signal peaks, the one or more unexpected cardiac signal peaks having an opposite polarity relative to a polarity of one or more cardiac signal peaks indicative of capture or intrinsic activation; and determining that the cardiac response classification is possibly erroneous if the unexpected signal content is detected, wherein at least one of delivering, classifying, and determining is implemented at least in part by circuitry.

2. The method of claim 1, wherein:

classifying the cardiac pacing response comprises:

detecting one or more cardiac signal peaks indicative of capture; and classifying the cardiac pacing response as capture based on the one or more detected cardiac signal peaks; and sensing for the unexpected signal content comprises sensing for one or more unexpected cardiac signal peaks, each of the one or more unexpected cardiac signal peaks having an opposite polarity relative to a polarity of a corresponding one of the one or more cardiac signal peaks indicative of capture.

3. The method of claim 1, wherein:

classifying the cardiac pacing response comprises:

detecting one or more cardiac signal peaks indicative of intrinsic activation; and classifying the cardiac pacing response as noncapture with intrinsic activation based on the one or more detected signal peaks; and sensing for the unexpected signal content comprises sensing for one or more unexpected cardiac signal peaks, each of the one or more unexpected cardiac signal peaks having an opposite polarity relative to a polarity of a corresponding one of the one or more cardiac signal peaks indicative of intrinsic activation.

4. The method of claim 1, wherein sensing the cardiac signal comprises sensing for cardiac signal behavior in one or more detection windows.

5. The method of claim 4, wherein detection windows has a finite time range and a finite amplitude range.

6. The method of claim 1, wherein sensing for the unexpected signal behavior comprises sensing for the unexpected cardiac signal behavior in one or more noise detection windows.

7. The method of claim 6, wherein each of the one or more noise detection windows has a finite time range and a finite amplitude range.

8. The method of claim 1, wherein:

sensing the cardiac signal comprises sensing for cardiac signal behavior indicative of a cardiac pacing response in one or more classification detection windows; and sensing for the unexpected signal content comprises sensing for the unexpected signal content in one or more noise detection windows, each noise detection window associated with a particular one of the one or more classification windows.

9. The method of claim 8, further comprising:

forming the one or more classification detection windows, each of the one or more classification detection windows formed based on one or more cardiac signals representative of a particular type of cardiac pacing response; and forming the one or more noise detection windows, each of the one or more noise detection windows formed in part based on a corresponding one of the classification detection windows.

10. The method of claim 9, further comprising:

adapting the one or more classification detection windows based on one or more additional cardiac signals indicative of the particular type of cardiac pacing response; and adapting the one or more noise detection windows based on a corresponding one of the one or more adapted classification windows.

11. The method of claim 8, further comprising:

forming the one or more classification detection windows, each of the one or more classification detection windows formed based on one or more cardiac signals representative of a particular type of cardiac pacing response; and forming the one or more noise detection windows, each of the one or more noise detection windows formed in part based on a feature of the sensed cardiac signals.

12. The method of claim 1, further comprising initiating a fusion/noise management process if the cardiac response classification is determined to be at least one of a fusion beat, an indeterminate response, and possibly erroneous.

13. The method of claim 1, wherein the classifying classifies the cardiac response based on at least one first feature of the sensed cardiac signal, and the unexpected signal content includes at least one second feature of the sensed cardiac signal, the unexpected signal content being inconsistent with capture and intrinsic activation if the at least one first and second features are collectively inconsistent with capture and intrinsic activation.

14. A cardiac rhythm management device, comprising:

a pulse generator configured to deliver pacing pulses to a heart chamber;

a sensing circuit configured to sense cardiac signals of the heart chamber, the sensed cardiac signals respectively associated with the pacing pulses; and a cardiac response classification processor, the processor coupled to the sensing circuit and configured to classify a cardiac response to a pacing pulse based on a sensed cardiac signal associated with the pacing pulse and to determine that the cardiac response classification is possibly erroneous if unexpected signal content is detected in the sensed cardiac signal, the cardiac response classification is one of a plurality of expected cardiac responses that the processor is configured to classify including capture, fusion, and intrinsic activation, and wherein the unexpected signal content is inconsistent with one or more of capture, fusion, and intrinsic activation.

15. The device of claim 14, wherein the processor is configured to classify the cardiac pacing response based on one or more cardiac signal peaks indicative of the cardiac pacing response and to determine that the cardiac pacing response classification is possibly erroneous based on one or more unexpected cardiac signal peaks.

16. The device of claim 14, wherein the processor is configured to classify the cardiac pacing response as a particular type of cardiac pacing response based on one or more peaks of the cardiac signal detected in one or more classification detection windows and the processor is configured to determine that the cardiac response classification is possibly erroneous if one or more unexpected cardiac signal peaks are detected in one or more noise detection windows.

17. The device of claim 16, wherein the processor is configured to form the one or more classification detection windows and the one or more noise detection windows.

18. The device of claim 16, wherein the processor is configured to adapt the one or more classification detection windows and the one or more noise detection windows.

19. The device of claim 16, wherein each of the one or more classification detection windows has a finite time range and a finite amplitude range.

20. The device of claim 16, wherein each of the one or more noise detection windows has a finite time range and a finite amplitude range.

21. The device of claim 14, wherein the processor is configured to classify the cardiac pacing response as capture based on the sensed cardiac signal and to determine that the captured response classification is possibly erroneous based on the unexpected signal content.

22. The device of claim 14, wherein the processor is configured to determine that the cardiac response classification is possibly erroneous based on the unexpected signal content comprising one or more of unexpected signal peaks having an opposite polarity relative to a polarity of one or more cardiac signal peaks indicative of capture or intrinsic activation.

23. The device of claim 14, wherein the processor is configured to classify the cardiac pacing response as noncapture with intrinsic activation based on the sensed cardiac signal and to determine that the noncapture with intrinsic activation response classification is possibly erroneous based on the unexpected signal content.

24. The device of claim 14, wherein the processor is configured to control delivery of a first pacing pulse to the heart chamber, determine that the cardiac response associated with the pacing pulse is at least one of fusion, indeterminate, and possibly erroneous, deliver one or more pacing pulses to the heart chamber if the cardiac response associated with the first pacing pulse is at least one of fusion, indeterminate, and possibly erroneous, the one or more pacing pulses having an energy greater than the first pacing pulse, the processor further configured to determine a cardiac response associated with each of the one or more pacing pulses, and to continue delivery of the one or more pacing pulses if the cardiac response to the one or more pacing pulses is at least one of fusion, indeterminate, and possibly erroneous.

25. The device of claim 24, wherein the processor is configured to terminate delivery of the one or more pacing pulses if the cardiac response to at least one of the one or more pacing pulses is classified as capture.

26. The device of claim 14, wherein the processor is configured to classify the cardiac response to the pacing pulse based on the cardiac signal sensed in a classification interval following the pacing pulse and the processor is configured to detect noise in a noise interval following the classification interval.

27. The device of claim 14, wherein the processor is configured to classify the cardiac response based on at least one first feature of the sensed cardiac signal, and the unexpected signal content includes at least one second feature of the sensed cardiac signal, the unexpected signal content being inconsistent with capture and intrinsic activation if the at least one first and second features are collectively inconsistent with capture and intrinsic activation.

28. A system for detecting cardiac signal noise during capture verification, comprising:
a pulse generator for delivering a pacing pulse to a heart chamber;
a sensing circuit for sensing a cardiac signal associated with the pacing pulse;
means for classifying a cardiac response to the pacing pulse based on the sensed cardiac signal using one or more classification detection windows, the cardiac response classification being one of a plurality of expected cardiac responses including capture and intrinsic activation;
means for sensing for unexpected signal content in the cardiac signal using one or more noise detection windows, the unexpected signal content being inconsistent with capture and intrinsic activation; and
means for determining that the cardiac response classification is possibly erroneous if the unexpected signal content is detected, wherein the one or more classification detection windows are different from the one or more noise detection windows.

29. The system of claim 28, wherein
the means for classifying classifies the cardiac response using one or more classification detection windows, each of the one or more classification detection windows formed based on one or more cardiac signals representative of a particular type of cardiac pacing response; and
the means for sensing senses for unexpected signal content using one or more noise detection windows, each of the one or more noise detection windows formed in part based on a corresponding one of the classification detection windows.

30. The system of claim 29, further comprising:
means for adapting the one or more classification detection windows based on one or more additional cardiac signals indicative of the particular type of cardiac pacing response; and
means for adapting the one or more noise detection windows based on a corresponding one of the one or more adapted classification windows.

31. The system of claim 29, wherein each of the one or more classification detection windows has a finite time range and a finite amplitude range.

32. The system of claim 29, wherein each of the one or more noise detection windows has a finite time range and a finite amplitude range.

33. The system of claim 28, wherein:
the means for classifying classifies the cardiac response using one or more classification detection windows, each of the one or more classification detection windows formed based on one or more cardiac signals representative of a particular type of cardiac pacing response; and
the means for sensing senses for unexpected signal content using one or more noise detection windows, each of the one or more noise detection windows formed in part based on a feature of the sensed cardiac signals.

34. The system of claim 28, further comprising means for initiating a fusion/noise management process if the cardiac response classification is determined to be at least one of a fusion beat, an indeterminate response, and possibly erroneous.

35. The system of claim 28, wherein the classifying means classifies the cardiac response based on at least one first feature of the sensed cardiac signal, and the unexpected signal content includes at least one second feature of the sensed cardiac signal, the unexpected signal content being inconsistent with capture and intrinsic activation if the at least one first and second features are collectively inconsistent with capture and intrinsic activation.

* * * * *

UNITED STATES PATENT AND TRADEMARK OFFICE
CERTIFICATE OF CORRECTION

PATENT NO. : 7,765,004 B2
APPLICATION NO. : 11/116565
DATED : July 27, 2010
INVENTOR(S) : Stalsberg et al.

It is certified that error appears in the above-identified patent and that said Letters Patent is hereby corrected as shown below:

In the Specification:

Col. 6, line 55: "7,319,900, now" should read --7,319,900,--.

Col. 18, line 62: "2004/0230229" should read --2004/0230230--.

Signed and Sealed this

Thirtieth Day of November, 2010

David J. Kappos
*Director of the United States Patent and Trademark Office*